(12) United States Patent
Copland

(10) Patent No.: US 11,877,797 B2
(45) Date of Patent: Jan. 23, 2024

(54) OPTICAL MEASUREMENT SYSTEMS AND PROCESSES WITH FIXATION TARGET HAVING CYLINDER COMPENSATION

(71) Applicant: AMO Development, LLC, Irvine, CA (US)

(72) Inventor: Richard J. Copland, Albuquerque, NM (US)

(73) Assignee: AMO Development, LLC, Irvine, CA (US)

(*) Notice: Subject to any disclaimer, the term of this patent is extended or adjusted under 35 U.S.C. 154(b) by 470 days.

(21) Appl. No.: 17/102,413

(22) Filed: Nov. 23, 2020

(65) Prior Publication Data
US 2021/0186321 A1 Jun. 24, 2021

Related U.S. Application Data

(60) Provisional application No. 62/953,158, filed on Dec. 23, 2019.

(51) Int. Cl.
*A61B 3/00* (2006.01)
*A61B 3/10* (2006.01)
(Continued)

(52) U.S. Cl.
CPC .......... *A61B 3/0091* (2013.01); *A61B 3/0025* (2013.01); *A61B 3/0041* (2013.01);
(Continued)

(58) Field of Classification Search
CPC ... A61B 3/0091; A61B 3/0025; A61B 3/0041; A61B 3/1015; A61B 3/103; A61B 3/14; A61B 3/102
(Continued)

(56) References Cited

U.S. PATENT DOCUMENTS

| | | |
|---|---|---|
| 5,777,719 A | 7/1998 | Williams et al. |
| 6,550,917 B1 | 4/2003 | Neal et al. |

(Continued)

FOREIGN PATENT DOCUMENTS

| | | |
|---|---|---|
| AU | 2002305262 B2 | 1/2007 |
| AU | 2007200139 A1 | 2/2007 |

(Continued)

OTHER PUBLICATIONS

Marcos S., et al., "The Depth-of-Field of the Human Eye from Objective and Subjective Measurements," Vision Research, Jun. 1999, vol. 39 (12), pp. 2039-2049.

(Continued)

*Primary Examiner* — Mohammed A Hasan
(74) *Attorney, Agent, or Firm* — Johnson & Johnson Surgical Vision, Inc.

(57) ABSTRACT

A system includes: a first movable stage which is movable with respect to an eye of a subject; a second movable stage mounted on the first movable stage, wherein the second movable stage is movable with respect to the first movable stage; a fixation target disposed on the second movable stage; and an optical system disposed in an optical path between the fixation target and the eye, wherein the optical system is configured for projecting the fixation target upon the eye to accommodate the eye. The optical system includes a Stokes cell in the optical path between the fixation target and the eye. The optical system non-telecentrically projects the fixation target upon the eye.

20 Claims, 16 Drawing Sheets

(51) Int. Cl.
*A61B 3/103* (2006.01)
*A61B 3/14* (2006.01)

(52) U.S. Cl.
CPC ............ *A61B 3/103* (2013.01); *A61B 3/1015* (2013.01); *A61B 3/14* (2013.01); *A61B 3/102* (2013.01)

(58) Field of Classification Search
USPC ........................................................ 351/221
See application file for complete search history.

(56) References Cited

U.S. PATENT DOCUMENTS

| | | | |
|---|---|---|---|
| 6,575,572 B2 | 6/2003 | Lai et al. | |
| 7,281,798 B2 | 10/2007 | Hanebuchi | |
| 7,520,613 B2 | 4/2009 | Saito et al. | |
| 7,537,341 B2 | 5/2009 | Saito et al. | |
| 7,540,614 B2 | 6/2009 | Kawashima et al. | |
| 7,780,291 B2 | 8/2010 | Saito et al. | |
| 7,942,527 B2 | 5/2011 | Olivier et al. | |
| 7,980,699 B2 | 7/2011 | Neal et al. | |
| 2004/0075811 A1* | 4/2004 | Liberman | A61H 5/00 351/203 |
| 2004/0218147 A1 | 11/2004 | Hayashi et al. | |
| 2006/0244911 A1 | 11/2006 | Shimizu et al. | |
| 2010/0123873 A1* | 5/2010 | Raymond | A61B 3/1015 351/212 |
| 2011/0149239 A1* | 6/2011 | Neal | A61B 3/103 351/205 |
| 2013/0208244 A1* | 8/2013 | Sakagawa | A61B 3/103 351/205 |
| 2016/0073868 A1* | 3/2016 | Raymond | A61B 3/103 351/246 |

FOREIGN PATENT DOCUMENTS

| | | | |
|---|---|---|---|
| EP | 3520678 A1 * | 8/2019 | ........... A61B 3/0091 |
| EP | 3520678 A1 | 8/2019 | |
| WO | 0160241 A1 | 8/2001 | |
| WO | 2008144168 A2 | 11/2008 | |
| WO | 2017059291 A1 | 4/2017 | |
| WO | WO-2017059291 A1 * | 4/2017 | ........... A61B 3/0025 |

OTHER PUBLICATIONS

Mejia-Barbosa Y., et al., "Object Surface for Applying A Modified Hartmann Test to Measure Corneal Topography," Applied Optics, Nov. 1, 2001, vol. 40 (31), pp. 5778-5786.

Yao P., et al., "Objective Depth-of-Focus Is Different From Subjective Depth-of-Focus and Correlated With Accommodative Microfluctuations," Vision Research, Jun. 2010, vol. 50 (13), pp. 1266-1273.

* cited by examiner

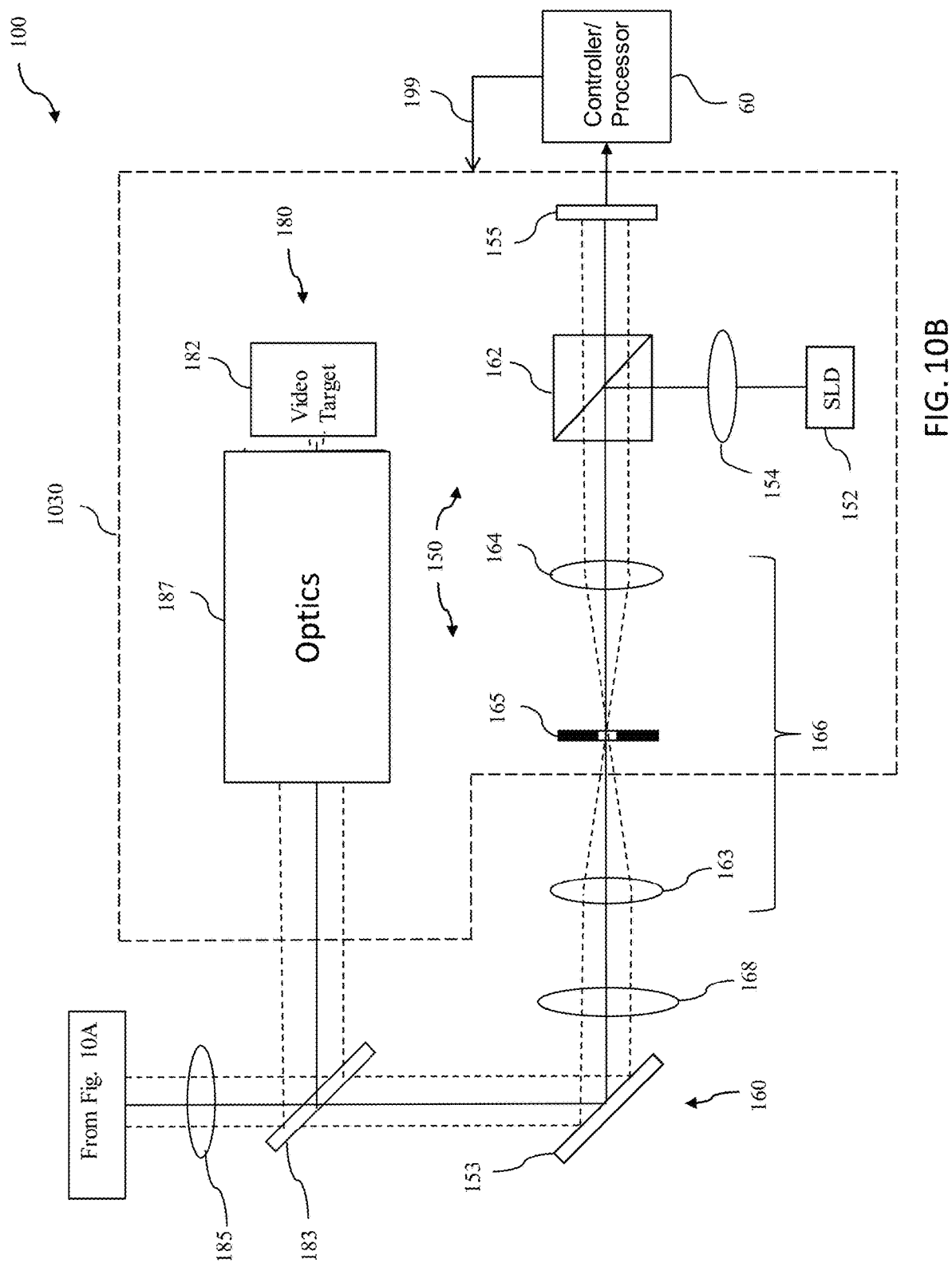

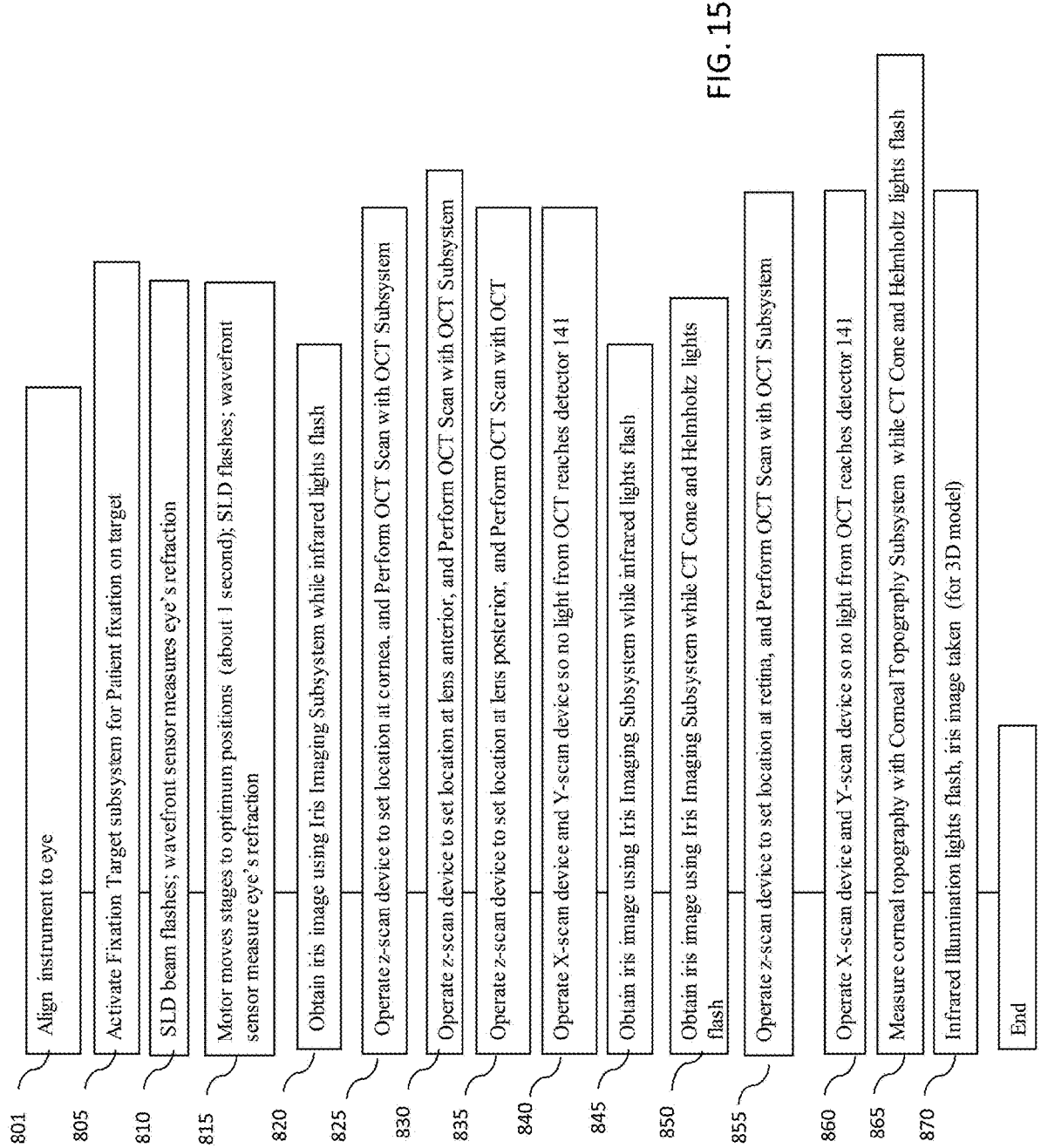

OPTICAL MEASUREMENT SYSTEMS AND PROCESSES WITH FIXATION TARGET HAVING CYLINDER COMPENSATION

CROSS-REFERENCES TO RELATED APPLICATIONS

This application claims the benefit under 35 U.S.C. § 119(e) of U.S. Provisional Patent Application No. 62/953,158, filed Dec. 23, 2019, which is incorporated herein by reference in its entirety.

TECHNICAL FIELD

Embodiments of this invention pertain to optical measurement equipment, and more particularly, to optical measurement systems and processes which include fixation targets for causing a subject's eye to accommodate during measurement.

BACKGROUND

Autorefractors and aberrometers (e.g., wavefront aberrometers) measure the refraction of a subject's eye using infrared light. It is desirable that the eye relax accommodation while the refraction is being measured to avoid an unknown change in the eye's focal power during the measurement which can lead to errors or inaccuracy in the measured refraction. Accordingly, autorefractors and aberrometers typically employ a fixation target for a person to view while the refractive state of the eye is being measured. One purpose of the fixation target is to draw the focus of the eye to its most distant refractive state, and then beyond, to so-call "fog" the eye while the refraction is being measured. Under these conditions, the eye attempts to keep the target in focus by relaxing accommodation, which as noted above is desirable. A patient's most distant refraction is also used for planning refractive eye surgeries.

However, with conventional autorefractors and aberrometers, about ten percent of people do not fully relax accommodation in response to the presented target. Because autorefractors are not completely reliable in fully relaxing the accommodation of a significant percentage of patients' eyes, the resulting refraction measurements are often erroneous or inaccurate. Furthermore, because it is not known whether this issue has occurred or not with a patient, there is a lack of confidence or trust in the results for all patients. Experiments where eye glasses have been prescribed based on autorefractions alone have resulted in a high fraction of unhappy patients. This leads optometrists to prescribe eye glasses based on manifest refractions measured with a phoropter instead of using results produced by an autorefractor or aberrometer.

Accordingly, it would be desirable to provide a fixation target system which is more effective in drawing out the eye's refractive state and stimulating fully relaxed accommodation for a greater percentage of patients during refraction measurements with an autorefractor or aberrometer. It would also be desirable to provide an optical measurement instrument, such as an autorefractor or aberrometer, which includes such a fixation target system. It would be further desirable to provide an improved method of drawing out the eye's refractive state to produce fully relaxed accommodation for a greater percentage of patients.

SUMMARY OF THE INVENTION

In one aspect, a system comprises: a wavefront aberrometer configured to measure a refraction of an eye; at least one processor; a first movable stage, wherein the first movable stage is movable with respect to the eye under control of the at least one processor; a second movable stage mounted on the first movable stage, wherein the second movable stage is independently movable with respect to the first movable stage and with respect to the eye, under control of the at least one processor; a fixation target for presentation by the system to the eye to cause the eye to accommodate during a process of measuring the refraction of the eye, wherein the fixation target is disposed on the second movable stage; and an optical system disposed in an optical path between the fixation target and the eye, wherein the optical system includes: a first lens which is not disposed on the first stage or second stage, a second lens and a third lens, each disposed on the first stage and not disposed on the second stage, a fourth lens disposed on the second stage, and a Stokes cell disposed on the first stage in the optical path between the second lens and the third lens.

In some embodiments, the Stokes cell is disposed one focal length from the second lens.

In some embodiments, the focal length of the fourth lens is about one half the focal length of the third lens.

In some embodiments, at least one of the third lens and the fourth lens comprises one of a telephoto lens and a retrofocus lens, including a weaker negative element combined with a stronger positive element.

In some embodiments, the system further comprises a video display, wherein the fixation target is provided via the video display, and wherein the at least one processor is configured to electronically make a size of the fixation target on the video display smaller while moving the second movable stage away from the eye.

In some embodiments, the aberrometer comprises: a light source; a Shack-Hartmann wavefront sensor; and a pair of lenses arranged as a telescope and configured to deliver a probe beam to the eye and returning light from the eye to the Shack-Hartmann wavefront sensor for measuring the refraction of the eye, wherein the Shack-Hartmann wavefront sensor and a first one of the pair of lenses is disposed on the first stage, and wherein a second one of the pair of lenses is not disposed on the first stage or the second stage.

In some embodiments, the fixation target comprises a circular pattern with a pair of cross hairs crossing at a middle of the circular pattern.

In another aspect, a method comprises: providing an arrangement comprising: a first movable stage, wherein the first movable stage is movable under control of the at least one processor with respect to an eye of a subject, a second movable stage disposed on the first movable stage, wherein the second movable stage is independently movable with respect to the first movable stage and with respect to the eye, under control of the at least one processor, a fixation target disposed on the second movable stage, and an optical system disposed in an optical path between the fixation target and the eye, wherein the optical system includes a Stoke cell and projects the fixation target upon the eye; the at least one processor moving the first movable stage with respect to the eye to a first stage position where the fixation target draws a focus of the eye to near its far point; stopping movement of the first movable stage with respect to the eye at the first stage position; and while the first movable stage is stopped, moving the second movable stage with respect to the first movable stage and the eye to a second stage position where the fixation target is moved away from the eye by an additional amount such that blur cues of the fixation target indicate to the subject that the fixation target is moving away from the eye at a same time that a size of an image of the fixation target on a retina of the eye decreases; measuring a cylinder of the eye; adjusting the Stokes cell to compensate for the measured cylinder of the eye; the at least one processor moving the first movable stage again with respect to the eye to the first stage position where the fixation target draws a focus of the eye to near its far point; again stopping movement of the first movable stage with respect to the eye at the first stage position; and while the first movable stage is stopped, moving the second movable stage again with respect to the first movable stage and the eye to a second stage position where the fixation target is moved away from the eye by an additional amount such that blur cues of the fixation target indicate to the subject that the fixation target is moving away from the eye at a same time that a size of an image of the fixation target on a retina of the eye decreases; measuring a refraction of the eye.

In s the optical system non-telecentrically projects the fixation target upon the eye.

In some embodiments, the method further comprises measuring the cylinder of the eye with a wavefront aberrometer having a wavefront sensor and a telescope, wherein a first lens of the telescope is disposed on the first stage and a second lens of the telescope is not disposed on the first stage or the second stage.

In some embodiments, the fixation target comprises a circular pattern with a pair of cross hairs crossing at a middle of the circular pattern.

In some embodiments, the optical system comprises: at least a first lens which is not disposed on the first stage or second stage, a second lens and a third lens, each disposed on the first stage and not disposed on the second stage, and a fourth lens disposed on the second stage, wherein the Stokes cell is disposed on the first stage in the optical path between the second lens and the third lens, and the method further comprises measuring the cylinder of the eye with a wavefront aberrometer having a wavefront sensor and a telescope, wherein a first lens of the telescope is disposed on the first stage and a second lens of the telescope is not disposed on the first stage or the second stage.

In some embodiments, the fixation target is provided via a video display, and wherein the method comprises electronically making a size of the fixation target on the video display smaller while moving the second movable stage to the second stage position.

In another aspect, a system comprises: a first movable stage, wherein the first movable stage is movable under control of the at least one processor with respect to an eye of a subject; a second movable stage mounted on the first movable stage, wherein the second movable stage is independently movable with respect to the first movable stage and with respect to the eye, under control of the at least one processor; a fixation target which is disposed on the second movable stage; and an optical system disposed in an optical path between the fixation target and the eye, wherein the optical system is configured for projecting the fixation target upon the eye to accommodate the eye, wherein the optical system includes a Stokes cell in the optical path between the fixation target and the eye, and wherein the optical system non-telecentrically projects the fixation target upon the eye.

In some embodiments, the optical system comprises at least a first lens which is not disposed on the first stage or second stage.

In some embodiments, the optical system comprises at least a second lens which is disposed on the second stage.

In some embodiments, the optical system comprises: at least a first lens which is not disposed on the first stage or second stage, a second lens and a third lens, each disposed on the first stage and not disposed on the second stage, and a fourth lens disposed on the second stage, wherein the Stokes cell is disposed on the first stage in the optical path between the second lens and the third lens.

In some embodiments, the Stokes cell is disposed one focal length from the second lens.

In some embodiments, the focal length of the fourth lens is about one half the focal length of the third lens.

In some embodiments, the system further comprises a video display, wherein the fixation target is provided via the video display, and wherein the at least one processor is configured to electronically make a size of the fixation target on the video display smaller while moving the second movable stage to the second stage position.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIGS. 10A and 10B illustrate together an assembly illustrating a suitable configuration and integration of an optical coherence tomographer subsystem, a wavefront aberrometer subsystem a corneal topographer subsystem, an iris imaging subsystem, a fixation target subsystem according to a non-limiting embodiment of the present invention.

FIG. 15 is a flowchart of an example embodiment of a method for measuring one or more characteristics of an eye, including wavefront aberrometry, corneal topography and OCT measurements at various locations with the eye along the axial length of the eye.

DETAILED DESCRIPTION

Exemplary embodiments of optical measurement systems and methods for measuring aberrations of an eye to illustrate various aspects and advantages of these devices and methods are described below. However, the principles involved in these devices and methods can be employed in a variety of other contexts, and that therefore the novel devices and method disclosed and claimed here should not be construed as being limited to the example embodiments described below.

U.S. Pat. No. 6,550,917, which is incorporated herein by reference, describes an instrument which includes a wavefront aberrometer, such as a Shack-Hartmann wavefront aberrometer that provides an adjustable telescope in the forward path from the light source to the eye and in the return path from the eye to the wavefront sensor. The adjustable telescope employs a moving stage to move one lens of the telescope with respect to the other, and a feedback arrangement whereby data from the wavefront sensor is employed to control a motor for the moving stage to move the stage to the desired location where the wavefront sensor sees collimated return light from the eye. The moving stage may be a common linear travel stage with stepper (or servo) motor drives and a position encoder. The position of the moving stage may be calibrated so the stage position corresponds to the refractive power of the eye being measured.

Figure 1:
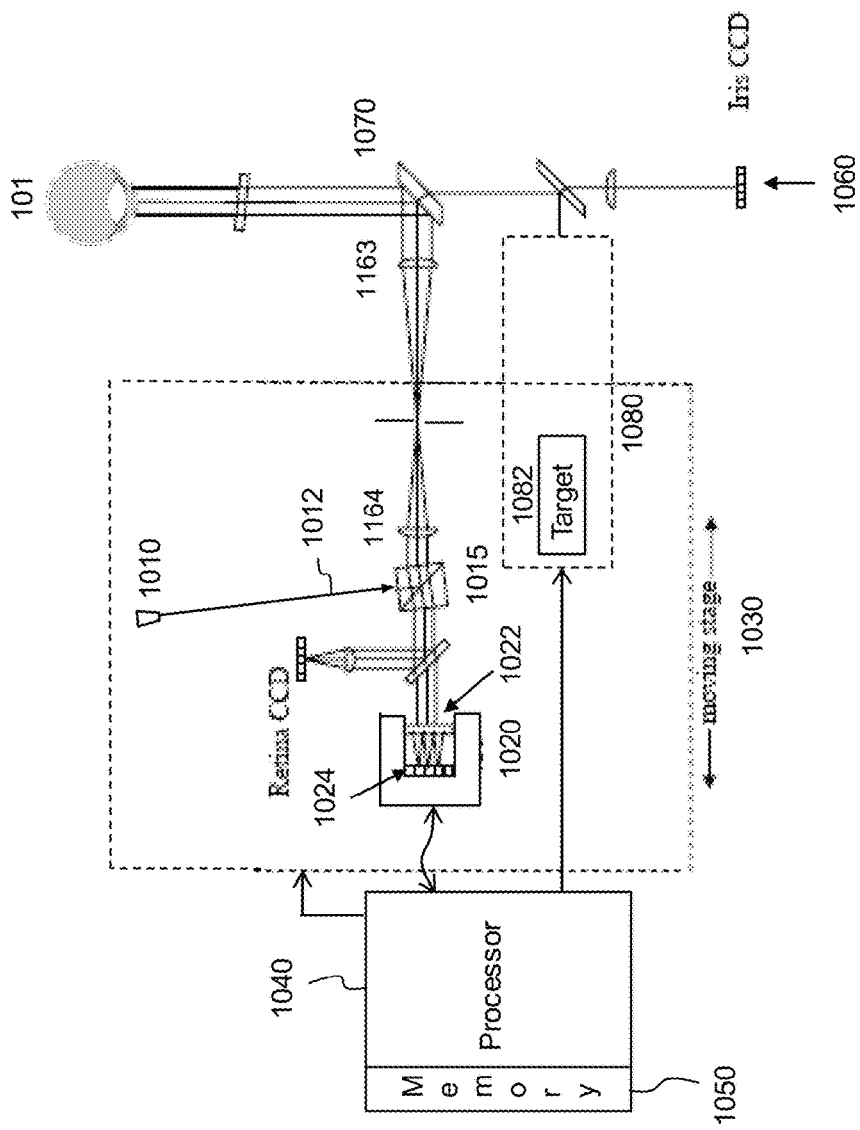
FIG. 1 illustrates an example embodiment of an optical measurement system which includes a wavefront aberrometer.

FIG. 1 illustrates an embodiment of a measurement instrument employing a wavefront sensor. Specifically, FIG. 1 illustrates a wavefront aberrometer 1000 for making wavefront measurements of a subject's eye 101. Among other components, wavefront aberrometer 1000 includes a probe beam light source 1010, a wavefront sensor 1020, and other components on a movable stage 1030, at least one processor 1040, memory 1050 associated with the at least one processor 1040, and an iris camera 1060.

Probe light beam source 1010 may comprise a laser, a laser diode, LED, or a super-luminescent diode (SLD), which may be connected to an optical fiber. For safety reasons, probe beam light source 1010 may be a pulsed light source, may be limited to a small power level, and may be outside the normal visual detection range, e.g. infrared.

Wavefront sensor 1020 is a Shack-Hartmann wavefront sensor. In other embodiments, a shearing interferometer or a Moiré deflectometer may be employed as a wavefront sensor. Wavefront sensor 1020 includes a lenslet array 1022 and a detector array (also known as a "pixel array") 1024. Wavefront data from detector array 1024 is supplied to processor 1040 and associated memory 1050 to execute one or more algorithms to determine a wavefront of a light beam received from the eye 101. Beneficially, processor 1040 may perform these algorithms in accordance with instructions stored in memory 1050. The operation of a Shack-Hartmann wavefront sensor in a wavefront aberrometer such as wavefront aberrometer 1000 may be understood with reference to U.S. Pat. No. 6,550,917, which is incorporated by reference, and will not be repeated here.

Wavefront aberrometer 1000 includes an optical imaging system comprising a telescope having a pair of lenses 1163 and 1164, and a dynamic range limiting aperture 1165, for example in an optical screening structure.

Processor 1040 controls the operation of wavefront aberrometer 1000 and can receive image data from wavefront sensor 1020 to measure the refraction of eye 101, including high order aberrations. Processor 1040 may also control movement of movable stage 1030, as described in more detail below. Processor 1040 may include any suitable components, such as one or more microprocessors, one or more field-programmable gate array (FPGA), and one or more memory storage devices.

Beneficially, wavefront sensor 1020 operates in conjunction with processor 1040 and associated memory 1050 to perform wavefront measurements on eye 101 to measure, inter alia, a refraction of eye 101.

As explained above, it is desirable that eye 101 relax accommodation while the refraction is being measured to avoid an unknown change in the focal power of eye 101 during the measurement which can lead to errors in the measured refraction. Accordingly, wavefront aberrometer 1000 includes a fixation target 1082 which includes a fixation target 1082 for a person to view while the refractive state of eye 101 is being measured to draw the focus of eye 101 to its most distant refractive state, and then beyond, to fog eye 101 while the refraction is being measured.

Figure 2:
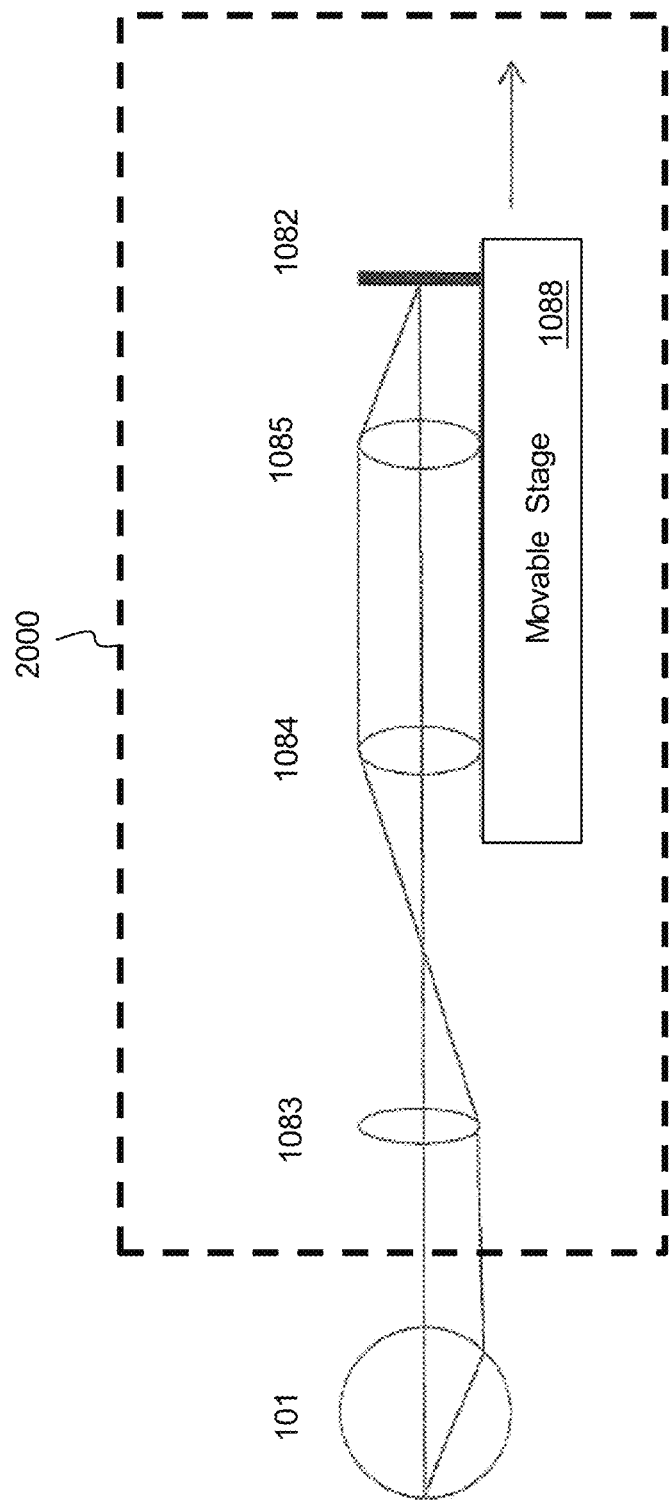
FIG. 2 illustrates an example of a fixation target system.

FIG. 2 illustrates an example of a fixation target system 2000. Fixation target system 2000 includes fixation target 1082, a first lens 1083, a second lens 1084, and a third lens 1085. Fixation target system 2000 includes a movable stage 1088 on which second lens 1084, third lens 1085 and fixation target 1082 are disposed or mounted. First lens 1083 is not disposed or mounted on movable stage 1088. In fixation target system 2000, eye 101 is located one focal length from first lens 1083.

In fixation target system 2000, the distance between second lens 1084 and third lens 1085 may be f2+f3, where f2 is the focal length of second lens 1084 and f3 is the focal length of third lens 1085. This is sometimes referred to as a Badal arrangement. In this arrangement, light rays that reach eye 101 are telecentric when they leave target 1082. That means the chief ray is parallel to the optical axis at target 1082. The chief ray is defined as the ray that leaves the edge of target 1082 and ultimately passes through the center of the stop of the system, which is the pupil of eye 101.

Movable stage 1088 may be referred to as a Badal stage, and in some embodiments may comprise the movable stage 1030 of wavefront aberrometer 1000 of FIG. 1. It is commonly noted that in a Badal arrangement, target 1082 appears to maintain constant size to a viewer as it moves away from eye 101 toward optical infinity. A key advantage of the arrangement is that a simple optical system can provide a similar visual appearance to a wide range of patients, from strong myopes of −20 Diopters through hyperopes up to +20 Diopters.

During a refraction measurement, the at least one processor 1040 moves movable stage 1088 and thereby moves target 1082 away from first lens 1083 to make target 1082 appear farther away from eye 101. Eye 101 attempts to keep target 1082 in focus by relaxing accommodation. In such a system the only cue that the patient or subject receives from eye 101 that target 1082 is moving more distant from eye 101 is that the image of target 1082 on the retina of eye 101 becomes blurred.

However, there is an underlying problem in the fixation target system 2000 for some eyes, namely those which have appreciable astigmatism. About ten percent of people do not fully relax accommodation in response to the presented target 1082 in fixation target system 2000, and people with strong astigmatism tend to respond the most poorly to fixation target system 2000.

Figure 3:
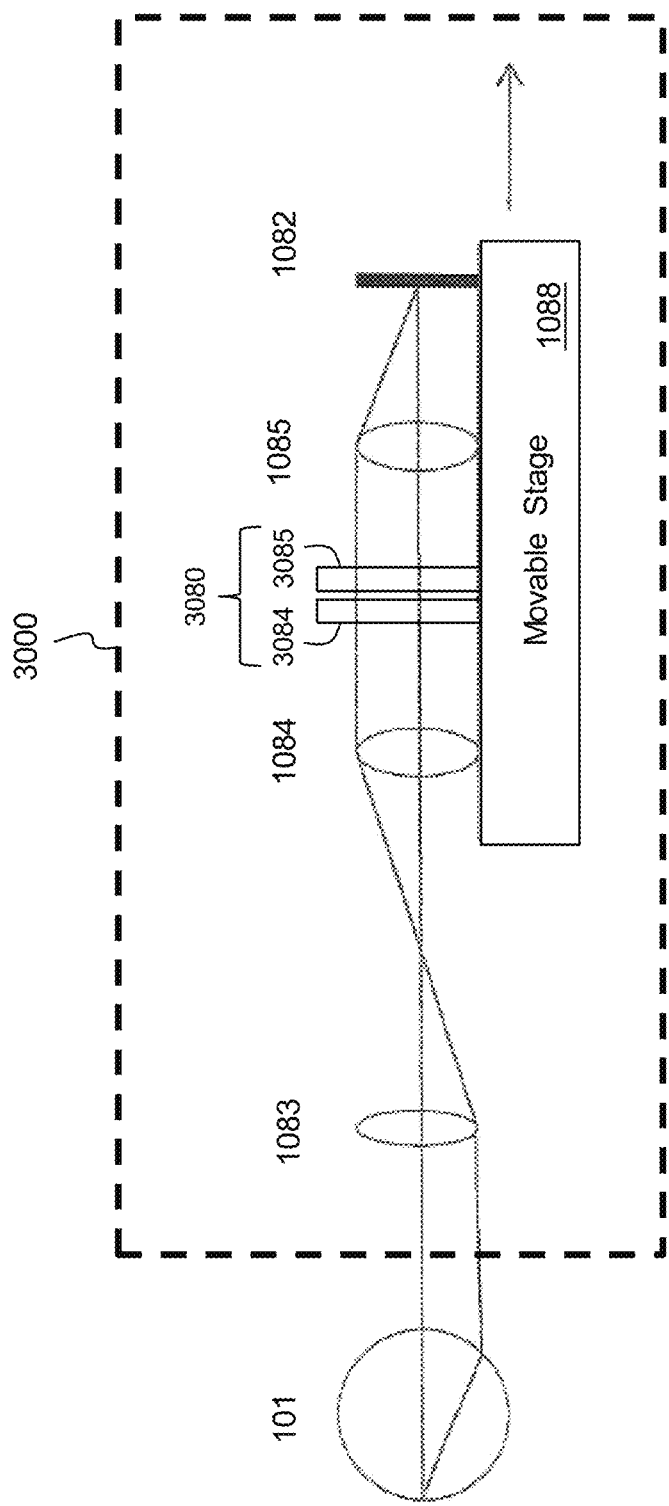
FIG. 3 illustrates another example of a fixation target system.

Accordingly, to address this, FIG. 3 illustrates another example of a fixation target system 3000. Fixation target system 3000 is like fixation target system 2000 with the exception that fixation target system 3000 includes a Stokes cell 3080. As used herein, a Stokes cell is defined as a device which includes two-cylinder lenses, each having a corresponding control mechanism for independently rotating the two lenses in an optical path and which can be used to compensate for the strength and axis of cylindrical error (astigmatism) in an eye.

Stokes cell 3080 includes a first cylinder lens 3084 and a second cylinder lens 3085, and corresponding motors for rotating cylinder lenses 3084 and 3085 under control of at least one processor (e.g., processor 1040) to compensate for astigmatism in eye 101.

Beneficially, in some embodiments Stokes cell 3080 is disposed or located one focal length away from second lens 1084. When disposed at this location, Stokes cell 3080 can correct the astigmatism of eye 101 without inducing any geometric distortions. If Stokes cell 3080 is located at any other location, then fixation target 1082 will appear to stretch along one dimension and the axis of stretching will rotate the orientations of the Stokes cell lenses 3084 and 3085.

The correction of astigmatism with Stokes cell 3080 seems to increase the effectiveness of target 1082 in relaxing accommodation in patients that have strong astigmatism.

Another issue with fixation target systems 2000 and 3000 occurs when movable stage 1088 is the movable stage 1030 of wavefront aberrometer 1000 of FIG. 1. In that case, movable stage 1088 is moved for optimum position of the telescope formed by lenses 1163 and 1162 with respect to wavefront sensor 1020. In that case, target 1082 cannot be independently moved for fogging.

Figure 4:
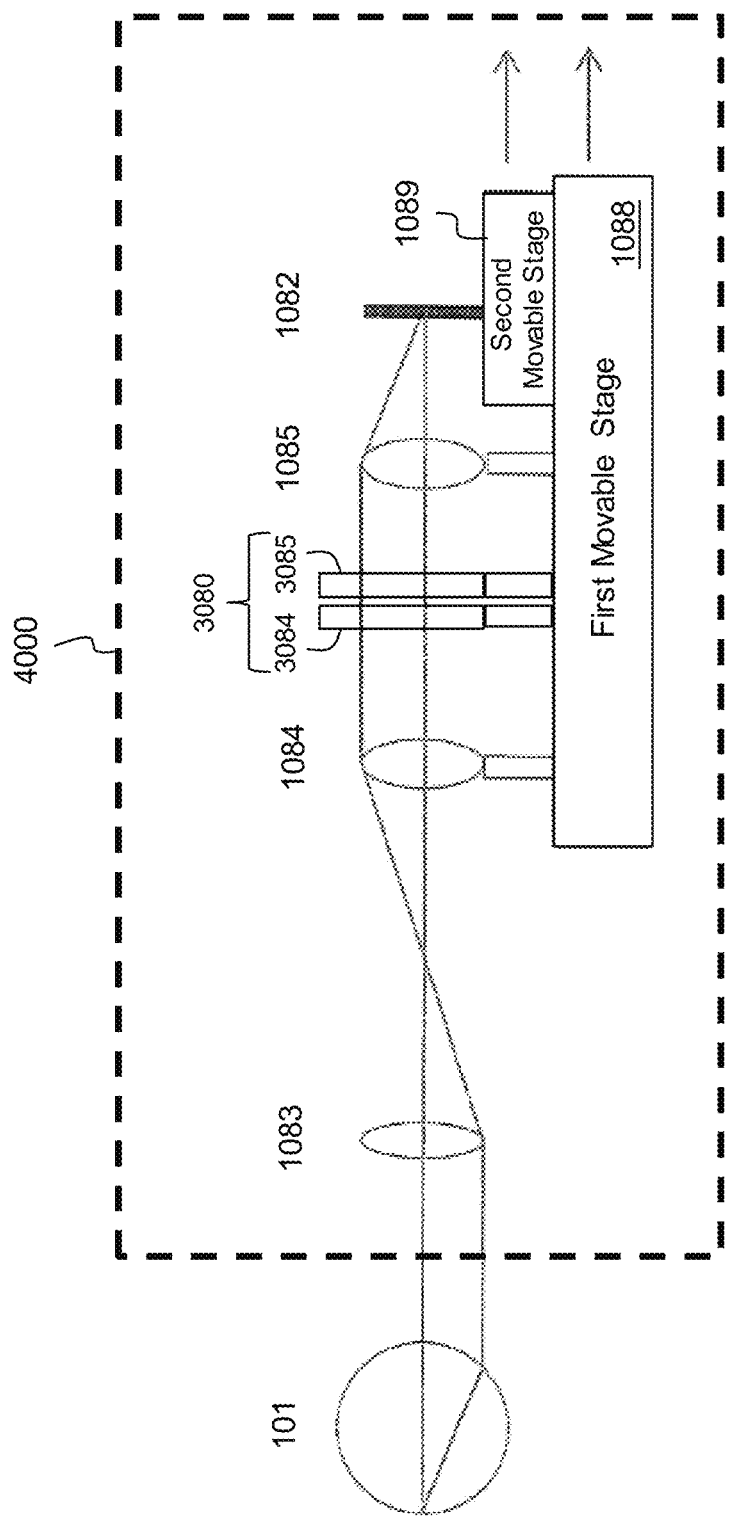
FIG. 4 illustrates yet another example of a fixation target system.

Accordingly, FIG. 4 illustrates yet another example of a fixation target system 4000 which allows independent movement of fixation target 1082. Fixation target system 4000 is like fixation target system 3000 with the exception that fixation target system 4000 includes a second movable stage 1089 on which target 1082 is disposed or mounted, wherein the second movable stage 1089 is disposed or mounted on first movable stage 1088. The at least one processor 1040 may independently move second movable stage 1089 with respect to first movable stage 1088 and eye 101. Second movable stage 1089 may be referred to as a fogging stage as its purpose is to move target 1082 further away from eye 101 once movable stage 1088 has placed target 1082 near the far focus point of eye 101, to fog eye 101.

First movable stage 1088 has a large range and is used to position target 1082 in the range for myopes to hyperopes; in some embodiments from −20 Diopter to +20 Diopters. Second movable stage 1089 has a smaller motion range to provide an independent fogging motion; in some embodiments of up to 3 Diopters.

However, there are some additional underlying problems in the fixation target systems 2000, 3000 and 4000 in that they create a visual experience that contains conflicting cues to a viewer. The brain knows that when something moves farther away, the apparent size of it should become smaller. So, the constant size of the image of target 1082 on the retina of eye 101 which is projected by the Badal arrangement of fixation target systems 2000, 3000 ad 4000 create conflicting visuals cue to eye 101. In the presence of these conflicting visual cues, some people's eyes will not relax accommodation completely.

However, the situation is a bit worse. Fogging or blurring target 1082 increases the apparent size of the image of target 1082 on the retina of eye 101 by a small amount. The effect is particularly pronounced for simple geometric targets, like white circular patterns on a black background. If we consider the target size appearance to be defined by the illuminated region on the retina, a Badal arrangement such as in fixation systems 2000, 3000 ad 4000 only maintain a constant target size for an eye with an infinitely small pupil.

As a practical example, consider an exemplary case where the focal lengths of lenses 1083, 1084 and 1085 are 73, 45 and 30 mm, respectively. Moving second movable stage 1089 by 4.0 mm under control of the at least one processor 140 creates a fogging amount on the eye of 1.5 diopters. The magnifications calculated using the chief ray would indicate the image of target 1082 on the retina of eye 101 remained constant when second movable stage 1089 moved. However, if we consider a reasonable sized eye pupil diameter of 4 mm, the size of the image of target 1082 on the retina increases by 15% due to the blurring effect.

Consequently, the overall image size is small when target 1082 is in focus on the retina. However, when target 1082 is fogged, the image of target 1082 forms in front of the retina and the rays expand as they continue and the overall illuminated region on the retina increases such that the image created is larger than when target 1082 is in focus on the retina due to the blurring. This creates the conflicting cues because the blur cues tell the brain that target 1082 has moved more distant from eye 101, but the size of the image of target 1082 on the retina is a cue which tells the brain that target 1082 has moved closer to eye 101.

For many people, these conflicting cues prevent eye 101 from fully relaxing its accommodation. Because autorefractors and aberrometers are not completely reliable in fully relaxing the accommodation of a significant percentage of patients' eyes, the resulting refraction measurements are often erroneous or inaccurate.

Figure 5:
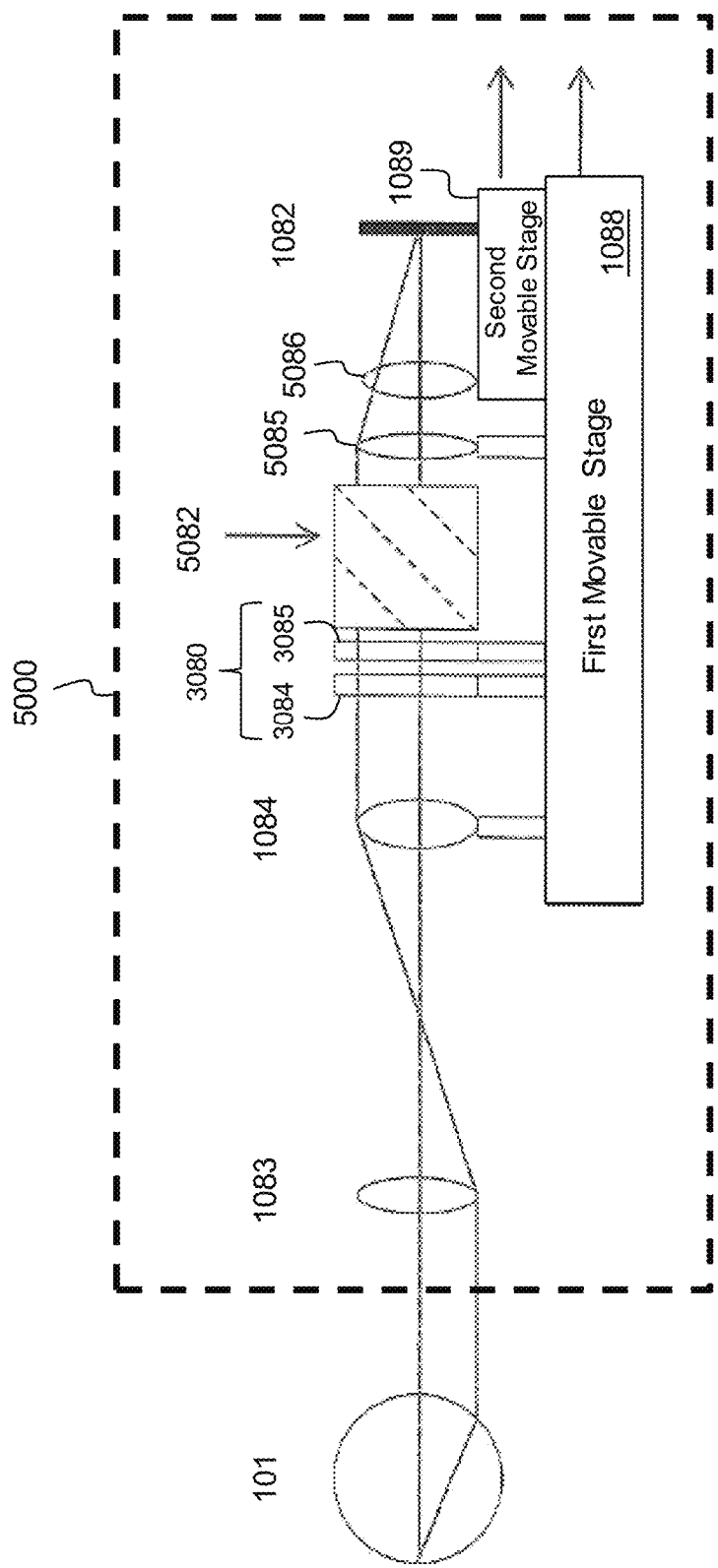
FIG. 5 illustrates still another example of a fixation target system.

To address one or more of these issues, the inventors have conceived and developed a fixation target system 5000 which is illustrated in FIG. 5.

Fixation target system 5000 includes a first lens 1083 and a first movable stage 1088. Fixation target system 5000 also includes second movable stage 1089 which is disposed or mounted on first movable stage 1088. Second lens 1084 and third lens 5085 are disposed or mounted on first movable stage 1088, while fourth lens 5086 and fixation target 1082 are both disposed or mounted on second movable stage 1089. First lens 1083 is not disposed or mounted on first movable stage 1088 or second movable stage 1089. In fixation target system 5000, eye 101 is located one focal length from first lens 1083.

In fixation target system 5000, light rays that reach eye 101 are non-telecentric when they leave target 1082. Accordingly, with a proper choice of lenses 5085 and 5086, it is possible to make the size of the image of fixation target 1082 which appears on the retina of eye 101 become smaller as fixation target is moved further away from eye 101, for example by moving second moving stage 1089.

Figure 6:
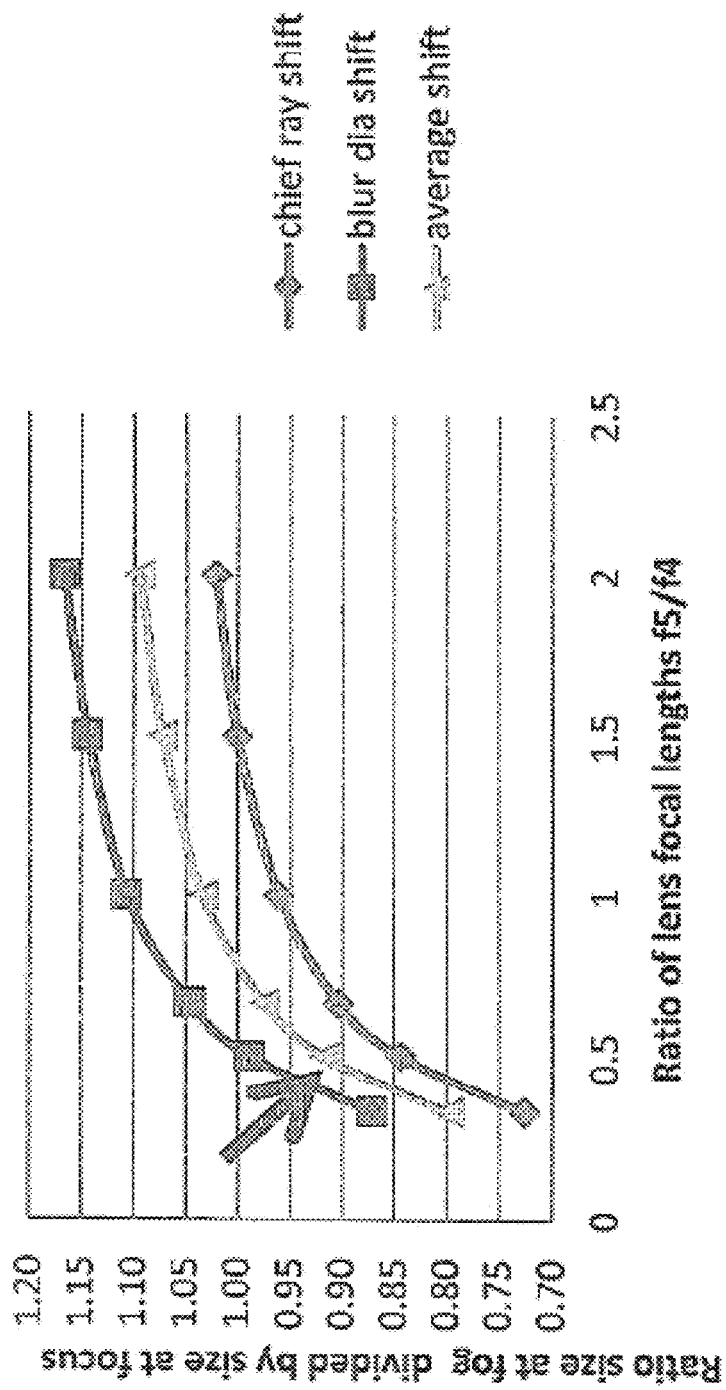
FIG. 6 is a plot illustrating how the size of the image of the target can be changed according to the focal lengths of lenses in the system of FIG. 5.

FIG. 6 is a plot illustrating how the size of the image of the target can be changed according to the focal lengths of lenses in the system of FIG. 5.

As an example, we assign lens focal lengths for first lens 1083 and second lens 1084 of 73 and 45 mm. For fourth lenses 5086 and 5085, we designate the focal lengths as f4 and f5 and we choose values that result in a combined focal length of 30 mm when the lenses are close, and the target appears in focus on the retina.

FIG. 6 shows how the size of the image changes when second movable stage 1089 moves to fog fixation target 1082 by 1.5 Diopters. The x-axis on FIG. 6 is the ratio of the lens focal lengths f5/f4. FIG. 6 shows that when the lens ratio is small, the target size decreases as second movable stage 1089 moves target 1082 more distantly from eye 101. When the lens ratio is large, the target size increases as second movable stage 1089 moves target 1082 away from eye 101. The conventional definition of target size has been defined by the chief ray. However, that ignores the fact that when target 1082 comes blurred, the blurring makes thin lines wider, which makes 1082 appear to become larger. The top line of FIG. 6 shows the target size considering the size increase due to blurring. However, the very outer rays of a blurred image will fall in intensity and may not contribute to the impression of target size. It is reasonable to expect that the impression of target size is somewhere in between the maximum blur diameter and the chief ray diameters, particularly for somewhat dim targets. In ophthalmic instruments sometimes dim targets are used to minimize shrinking of the pupil due to bright targets. This average value is plotted as the middle line in FIG. 6. This line best probably represents how the apparent size of target 1082 changes as second movable stage 1089 is moved. In FIG. 6, a large arrow has been drawn to point out a case that produces the desired optical effect. When second movable stage 1089 moves from fixation target 1082 being in focus, to providing 1.5 diopter fog for fixation target 1082, the average retinal image size shrinks to be about 92% of what it was when the target was in focus. For this specific case the lens focal lengths are f4=90 and f5=45 mm and the ratio f5/f4 is 0.5.

Because astigmatism may be compensated for and the visual cues are consistent with fixation target system 5000, a larger percentage of patient eyes 101 will fully relax accommodation during refraction measurements by wavefront aberrometer 1000.

Other arrangements of optics in lieu of the arrangement of first, second, third and fourth lenses 1083, 1084, 5085 and 5086 shown in FIG. 5 may create the situation that the rays leaving the target 1082 are non-telecentric, thereby producing the desirable result of a smaller image of target 1082 on the retina of eye 101 as target 1082 is moved further away from eye 101. However, fixation target system 5000 exemplifies a particularly simple arrangement which lends itself to good image quality.

In some embodiments, fixation target 1082 comprises a circular pattern with a pair of cross hairs crossing at a middle of the circular pattern.

In other embodiments, a fixation target system may include a video display disposed or mounted on the second movable stage, wherein the fixation target is provided via the video display, and wherein the at least one processor 1040 is configured to electronically make the size of the fixation target on the video display smaller while moving the second movable stage to the second stage position which is more distant from eye 101.

Figure 7:
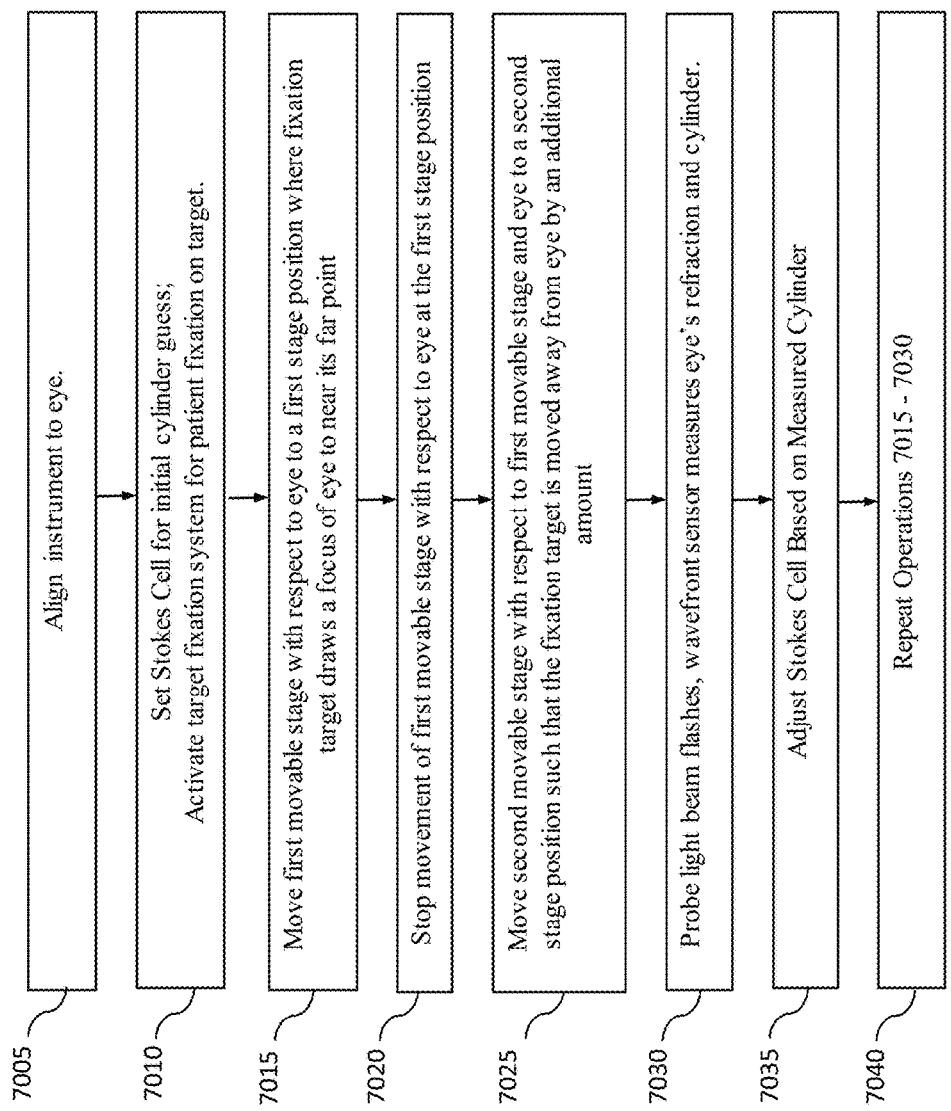
FIG. 7 is a flowchart of an example embodiment of a method of measuring one or more characteristics of an eye with a wavefront aberromoter.

FIG. 7 is a flowchart of an example embodiment of a method 7000 of measuring one or more characteristics of eye 101 with a wavefront aberrometer such as wavefront aberrometer 1000 and fixation target system 6000.

An operation 7005 includes aligning a measurement instrument, including the wavefront aberrometer 1000, to eye 101 to be measured.

An operation 7010 includes setting the lenses 3085 and 3085 of Stokes cell 3080 to compensate for an "initial guess" of the cylinder values (e.g., strength and axis) of eye 101, activating fixation target system 6000 for patient fixation on target 1082. In some embodiments, the "initial guess" may be based on an assumption that eye 101 has zero astigmatism. In other embodiments, the "initial guess" may be obtained from previous measurements of eye 101, for example during a previous eye examination. In still other embodiments, the "initial guess" may be obtained from physical measurements of the eye, for example using a corneal topographer and/or an optical coherence tomographer.

An operation 7015 includes the at least one processor 1040 moving first movable stage 1088 with respect to eye 101 to a first stage position where fixation target 1082 draws a focus of eye 101 to near its far point (e.g., within one diopter of its far point).

An operation 7020 includes stopping movement of first movable stage 1088 with respect to eye 101 at the first stage position.

An operation 7025 includes, while first movable stage 1088 is stopped, moving second movable stage 1089 with respect to first movable stage 1088 and eye 101 to a second stage position where fixation target 1082 is moved away from eye 101 by an additional amount (e.g., 1.5 diopters) such that blur cues of fixation target 1082 indicate to the subject that fixation target 1082 is moving away from eye 101 at a same time that a size of an image of fixation target 1082 on the retina of eye 101 decreases.

An operation 7030 includes flashing a probe light beam and causing wavefront sensor 1020 to measures refraction and cylinder values of eye 101. In some embodiments, only the cylinder values of eye 101 are measured the first time that operation 7030 is performed. In some embodiments, only the refraction of eye 101 is measured the second time that operation 7030 is performed (see operation 7040, below).

An operation 7035 includes adjusting Stokes cell 3080 (e.g., processor 1040 rotating lenses 3084 and 3085) based on the measured cylinder values of eye 101.

An operation 7040 includes repeating operations 7015 through 7030 after Stokes cell 3080 has been adjusted to compensate for the measured astigmatism of eye 101.

In some embodiments where the astigmatism of eye 101 is known apriori, then in operation 7010 Stokes cell 3080 is adjusted to compensate for the known astigmatism of eye 101, and operations 7035 and 7040 may be omitted. In that case, in some embodiments operation 7030 may only measure refraction of eye 101, without remeasuring the cylinder values.

The principles of wavefront aberrometer 1000 including a fixation target system such as fixation target system 5000, and an associated method of operation, as described above, may be applied to an optical measurement instrument which includes additional functionality, such as the ability to measure corneal topography and/or to make optical coherence tomography (OCT) measurements of interior structures of the eye. Embodiments of such an optical measurement instrument, and methods of operation thereof, will now be described.

Figure 8C:
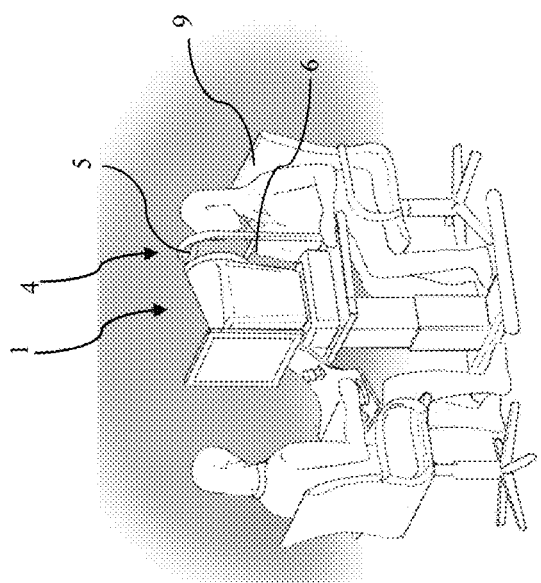
FIG. 8C illustrates a side perspective view showing an optical measurement system according to many embodiments.
Figure 8A:
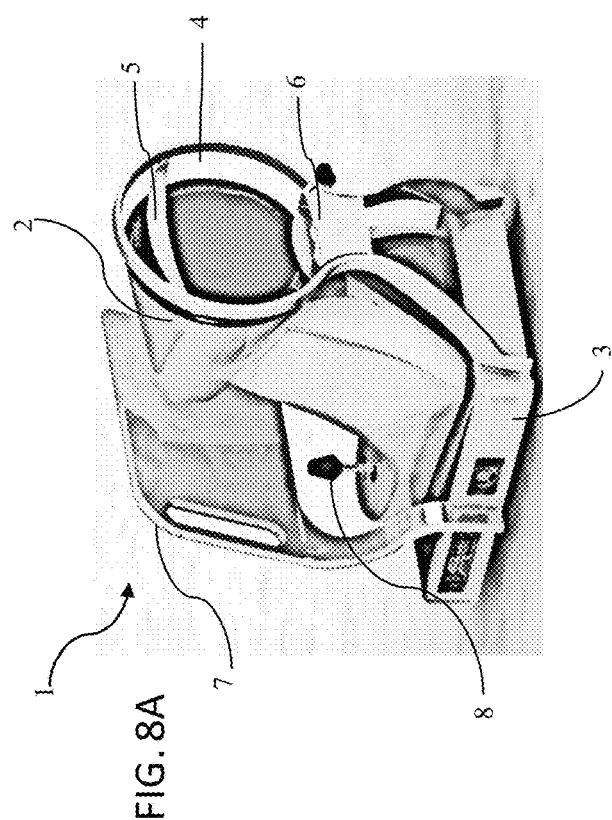
FIG. 8A illustrates a front perspective view showing an optical measurement system according to many embodiments.
Figure 8B:
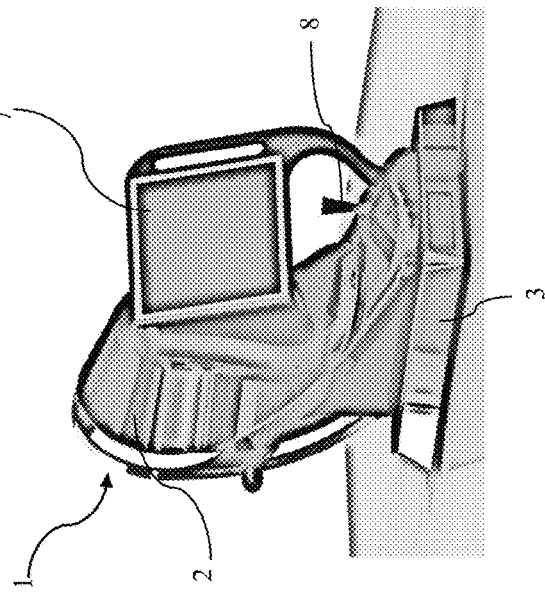
FIG. 8B illustrates a rear perspective view showing an optical measurement system according to many embodiments.

As shown in FIGS. 8A-8C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1 includes a main unit 2 which comprises a base 3 and includes many primary subsystems of many embodiments of the system 1. For example, externally visible subsystems include a touch-screen display control panel 7, a patient interface assembly 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by the system 1.

In one embodiment the patient interface includes a chin support 6 and/or a forehead rest 4 configured to hold the head of the patient in a single, uniform position suitably aligned with respect to the system 1 throughout the diagnostic measurement. As shown in FIG. 8C, the optical measurement system 1 may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, the system 1 may include external communication connections. For example, the system 1 can include a network connection (e.g., an RJ45 network connection) for connecting the system 1 to a network. The network connection can be used to enable network printing of diagnostic reports, remote access to view patient diagnostic reports, and remote access to perform system diagnostics. The system 1 can include a video output port (e.g., HDMI) that can be used to output video of diagnostic measurements performed by the system 1. The output video can be displayed on an external monitor for, for example, viewing by physicians or users. The output video can also be recorded for, for example, archival purposes. The system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed later for any suitable purpose such as, for example, printing from an external computer in the case where the user without access to network-based printing or for use during cataract surgery, including laser cataract surgery.

Figure 9:
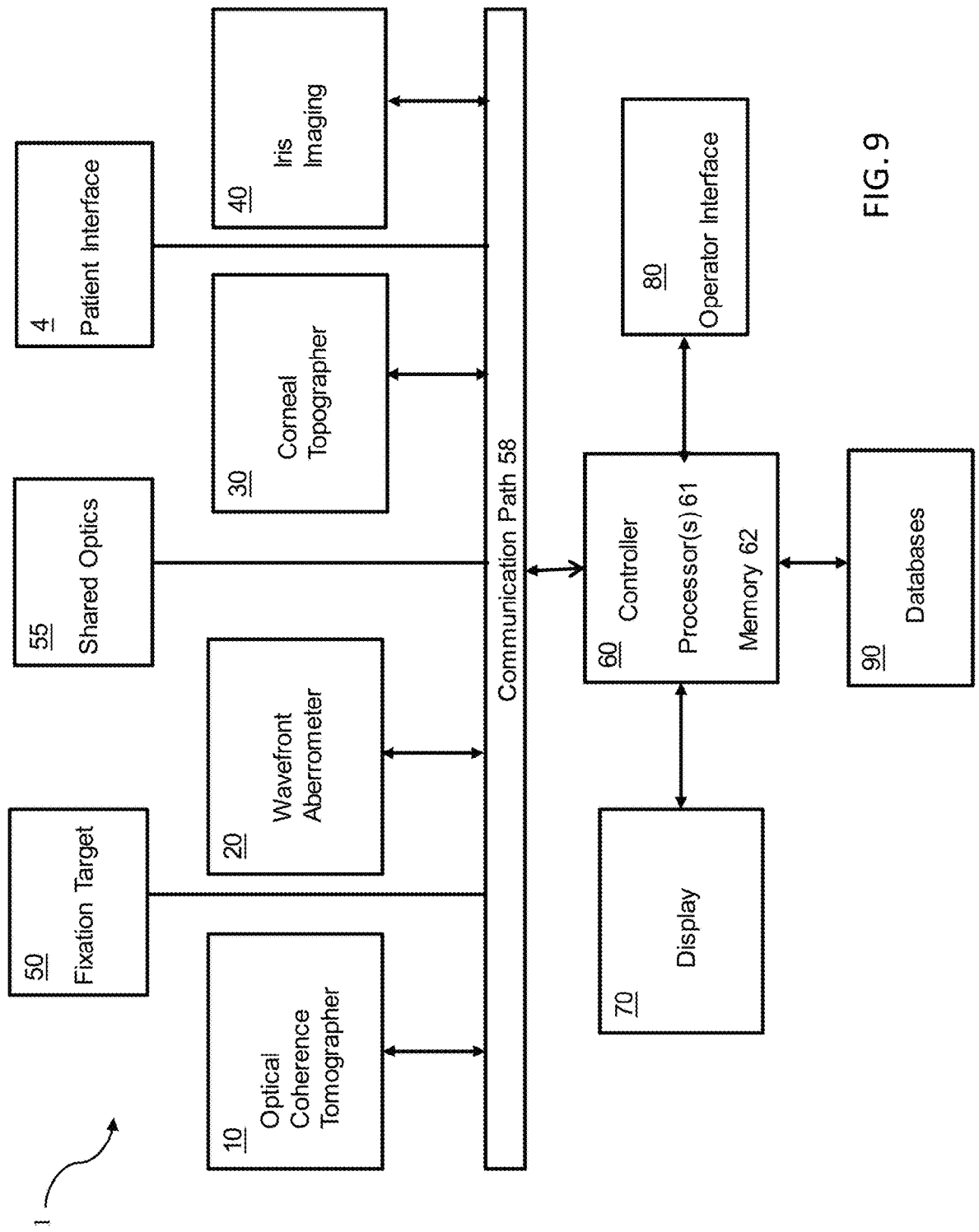
FIG. 9 is a block diagram of a system including an optical measurement instrument, and a position of an eye relative to the system according to one or more embodiments described herein which may be used by the optical measurement.

FIG. 9 is a block diagram of a system including an optical measurement instrument 1 according to one or more embodiments described herein. Optical measurement instrument 1 includes: an optical coherence tomographer (OCT) subsystem 10, a wavefront aberrometer subsystem 20, and a corneal topographer subsystem 30 for measuring one or more characteristics of a subject's eye. Optical measurement instrument 1 may further include an iris imaging subsystem 40, a fixation target subsystem 50, a controller 60, including one or more processor(s) 61 and memory 62, a display 70 and an operator interface 80. Optical measurement instrument 1 further includes a patient interface 4 for a subject to present his or her eye for measurement by optical measurement instrument 1.

The optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by the controller for several purposes, including, in some embodiment to program and control a subsequent laser-assisted surgical procedure. The spatial disposition of the structures of interest and/or of suitable matching geometric modeling can also be used to determine a wide variety of parameters.

As a non-limiting example, the system 1 can be configured to use a swept source OCT imaging system employing wavelengths of around 1060 nm with an 8 mm scan depth. The spatial disposition of the eye structures using optical coherence tomography should generally be measured while the patient is engaged with patient interface 4. The OCT scan depth may be between 8 and 50 mm, and the scan depth may be greater than about 24 mm or even 30 mm to achieve a full eyescan depth. The swept source wavelengths can be centered at wavelengths from 840 nm to 1310 nm.

Optical coherence tomographer subsystem 10 is only one example of an eye structure imaging subsystem which may be employed in optical measurement instrument 1. In other embodiments, a different eye structure imaging subsystem may be employed, for example a Scheimplug Imager, a fluorescence imager, a structured lighting imager, a wavefront tomographer, an ultrasound imager and a plenoptic imager.

The wavefront aberrometer subsystem 20 is configured to measure ocular aberrations, which may include low and high order aberrations, by measuring the wavefront emerging from the eye by, for example a Shack Hartman sensor.

The corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target system 50 is configured to control the patient's accommodation, as described above. In some embodiments, fixation target system 50 may be implemented by fixation target system 1080. In some embodiments, fixation target system 50 may be implemented by fixation target system 5000.

Images captured by the corneal topographer subsystem 10, the wavefront aberrometer 20, the optical coherence tomographer subsystem 30 or the camera 40 may be displayed with a display of the operator interface 80 of the optical measurement system 2 or the display 70 of the optical measurement system, respectively. The operator interface may also be used to modify, distort, or transform any of the displayed images.

The shared optics 55 provide a common propagation path that is disposed between the patient interface 4 and each of the optical coherence tomographer (OCT) subsystem 10, the wavefront aberrometer subsystem 20, the corneal topographer subsystem 30, and in some embodiments, the camera 40, and the fixation target system 50. In many embodiments, the shared optics 55 may comprise several optical elements, including mirrors, lenses and beam combiners to receive the emission from the respective subsystem to the patient's eye and, in some cases, to redirect the emission from a patient's eye along the common propagation path to an appropriate director.

The controller 60 controls the operation of the optical measurement instrument 1 and can receive input from any of the optical coherence tomographer (OCT) subsystem 10, the wavefront aberrometer subsystem 20, the corneal topographer subsystem 30 for measuring one or more characteristics of a subject's eye, the camera 40, the fixation target system 50, the display 70 and the operator interface 80 via the communication paths 58. The controller 60 can include any suitable components, such as one or more processor, one or more field-programmable gate array (FPGA), and one or more memory storage devices. In many embodiments, the controller 60 controls the display 70 to provide for user control over the laser eye surgery procedure for pre-cataract procedure planning according to user specified treatment parameters as well as to provide user control over the laser eye surgery procedure. The communication paths 58 can be implemented in any suitable configuration, including any suitable shared or dedicated communication paths between the controller 60 and the respective system components.

The operator interface 80 can include any suitable user input device suitable to provide user input to the controller 60. For example, the user interface devices 80 can include devices such as joystick 8, a keyboard or a touchscreen display 70.

Figure 10A:
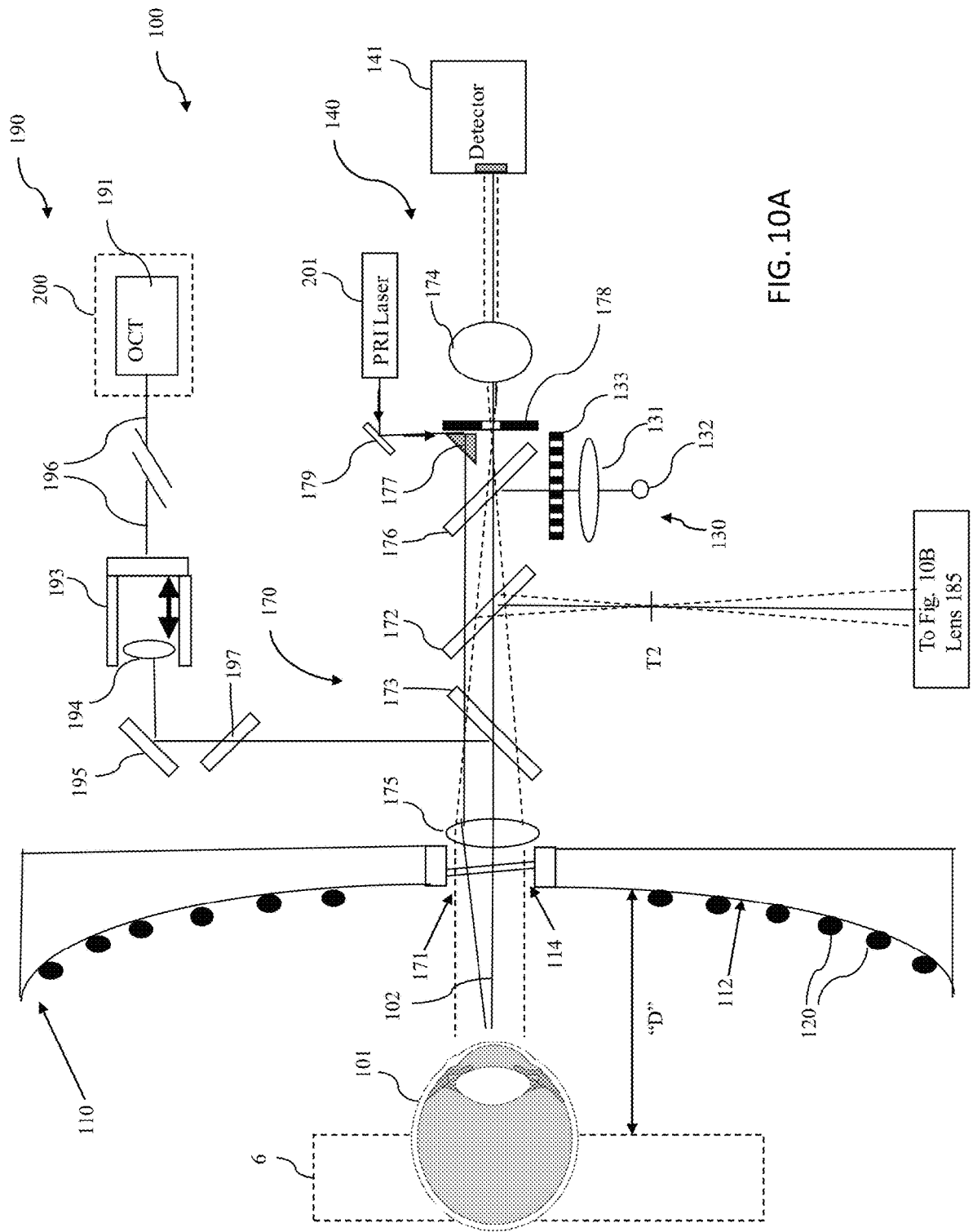

FIGS. 10A and 10B are simplified block diagrams illustrating an assembly 100 according to many embodiments which may be included in system 1. The assembly 100 is a non-limiting example of suitable configurations and integration of the optical coherence tomographer (OCT) subsystem 190, the wavefront aberrometer subsystem 150, the corneal topographer subsystem 140 for measuring one or more characteristics of a subject's eye, a camera 40, a fixation target subsystem 180 and the shared optics.

The shared optics generally comprise one or more components of a first optical system 170 disposed along a central axis 102 passing through the opening or aperture 114 of the structure 110. A first optical system 170 directs light from the various light sources along the central axis 102 towards the eye and establishes a shared or common optical path along which the light from the various light sources travel to the eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from the wavefront aberrometer subsystem 150 and comprises mirror 153, beam splitter 183 and lens 185.

Other configurations of the assembly 100 may be possible and may be apparent to a person of skill in the art.

The corneal topographer subsystem 140 comprises a structure 110 having a principal surface 112 with an opening or aperture 114 therein; a plurality of first (or peripheral) light sources 120 provided on the principal surface 112 of the structure 110; a Helmholz light source 130; and a detector, photodetector, or detector array 141.

In one embodiment, structure 110 has the shape of an elongated oval or "zeppelin" with openings or apertures at either end thereof. An example of such a structure is disclosed in Yob ani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 100, as illustrated in FIG. 10A.

In one embodiment where principal surface 112 is concave, principal surface 112 has the shape of a conical frustum. Alternatively, principal surface 112 may have a shape of hemisphere or some other portion of a sphere, with an opening or aperture therein. Also, alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 100 without being obstructed by the subject's nose. Of course, a variety of other configurations and shapes for principal surface 112 are possible.

In the embodiment of FIG. 10A, the plurality of first light sources 120 are provided on the principal surface 112 of structure 110 to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 100. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 10A).

In operation, a ray (solid line) from one of the first light sources 120 is reflected by the cornea and passes through optical system 170 (including aperture 178) to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered to not pass through the optical system 170. In similar fashion, light from the other first light sources 120 are imaged onto detector array 141 such that each one of first light sources 120 is imaged or mapped to a location on detector array 141 that may be correlated to a reflection location on the cornea of eye 100 and/or the shape of the cornea. Thus, detector array 141 detects the light spots projected thereon and provides corresponding output signals to a processor of controller 60 (FIG. 9). The processor determines the locations and/or shape of the light spots on detector array 141 and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two-dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 61 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 100. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, second light sources 132 are located off the central optical axis 102 of assembly 100, and light from second light sources 132 is directed toward optical element 171 by third beam splitter 176.

The operation of the topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 140 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141 and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflecton illuminator is configured to direct a disc of light toward a patient's eye, whereby the disc of light may be reflected from reflective surfaces within the eye, and the reflected light is transmitted by optical path 170 to detector 141. The pupil retroreflection illuminators may optionally be configured such that, when a patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

The wavefront aberrometer subsystem 150 of the assembly 100 comprises a third (probe light beam) light source 152 providing a probe light beam and a wavefront sensor 155. Wavefront aberrometer subsystem 150 may further comprise: a collimating lens 154; a polarizing beamsplitter 163; and an imaging system 166 comprising a first optical element, lens 163 and a second optical element, lens 164, and a dynamic-range limiting aperture 165 for limiting a dynamic range of light provided to wavefront sensor 155 to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is like a laser in that the light originates from a very small emitter area. However, unlike a laser, the spectral width of the SLD is very broad, about 40 nm. This tends to reduce speckle effects and improve the images that are used for wavefront measurements.

Wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows system 100 to provide a probe light beam into eye 101 to characterize its total ocular aberrations. Accordingly, third light source 152 supplies a probe light beam through polarizing beam splitter 162 to first beamsplitter 172 of optical system 170. First beamsplitter 172 directs the probe light beam through aperture 114 to eye 101. Beneficially, light from the probe light beam is scattered from the retina of eye 100, and at least a portion of the scattered light passes back through aperture 114 to first beamsplitter 172. First beamsplitter 172 directs the back scattered light back through beam splitter 172 to polarizing beamsplitter 183, mirror 153, adjustable focal length lens 179, and ultimately to wavefront sensor 155.

Wavefront sensor 155 outputs signals to a processor of controller/processor 60 which uses the signals to determine ocular aberrations of eye 101, including measuring the refraction of eye 101. Beneficially, controller/processor 60 may be able to better characterize eye 101 by considering the corneal topography of eye 101 measured by the corneal topography subsystem, which may also be determined by controller/processor 60 based on outputs of detector array 141, as explained above.

In operation of the wavefront aberrometer subsystem 150, light from light source 152 is collimated by lens 154. The light passes through light source polarizing beam splitter 162. The light entering light source polarizing beam splitter 162 is partially polarized. Polarizing beam splitter 162 reflects light having a first, S, polarization, and transmits light having a second, P, polarization so the exiting light is 100% linearly polarized. In this case, S and P refer to polarization directions relative to the hypotenuse in light source polarizing beam splitter 162.

The light from polarizing beamsplitter 162 travels through adjustable focal length lens 179 and passes through toward beam splitter 153, retaining its S polarization, and then travels through beamsplitter 183, optical element (e.g., lens) 185, beamsplitter 172 and 173, and quarter wave plate 171. Quarter wave plate 171 converts the light to circular polarization. The light then travels through aperture 114 in principal surface 112 of structure 110 to eye 101. Beneficially, the beam diameter on the cornea may be between 1 and 2 mm. Then the light travels through the cornea and focuses onto the retina of eye 101.

The focused spot of light becomes a light source that is used to characterize eye 101 with wavefront sensor 155. Light from the probe light beam that impinges on the retina of eye 101 scatters in various directions. Some of the light reflects back as a semi-collimated beam back towards assembly 100. Upon scattering, about 90% of the light retains its polarization. So, the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe light beam having the S polarization. This P polarized light then reflects off of first beamsplitter 172, and passes through optical element (e.g., lens) 185, beamsplitters 183 and 153, optical element (e.g., lens) 168 and reaches polarizing beamsplitter 162. Since the light is now P polarized relative the hypotenuse of polarizing beamsplitter 162, the beam is transmitted and then continues to imaging system 166 comprising first optical element 164 and second optical element (e.g., lens) 163. The beam is also directed through a dynamic-range limiting aperture 165 for limiting a dynamic range of light provided to wavefront sensor 155 to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to be processed by controller/processor 60 and analyzed to compute the refraction and aberrations of eye 101.

The comprises a pre-correction system which compensates the probe light beam 153 to be injected into eye 101 for aberrations in eye 101 by adding a desired pre-correction for the injected probe light beam 153 by adding defocus that just compensates for the spherical equivalent defocus of eye 101 which is being measured. Movable stage 1130 may be moved in response to control signal 199 which may be provided from controller/processor 60.

The same position of movable stage 1130 which corrects for the defocus aberrations of eye 101, also ensures that the returned light arrives at a wavefront sensor 155 collimated to within the dynamic range of wavefront sensor 155. Dynamic range limiting aperture 165 blocks any rays outside the angular dynamic range of the wavefront sensor 155 so that no mixing or measurement confusion occurs. When the wavefront sensor 155 is a Shack-Hartmann sensor, the focal spots cannot collide, interfere or cause confusion with adjacent focal spots.

Beneficially, controller/processor 60 moves movable stage 1130 to provide a desired characteristic to at least one of: probe light beam 153 injected into eye 101, or the light received by wavefront sensor 155 from the retina of eye 101.

The proper or desired adjusted focal length for movable stage 1130 may be determined in several ways. In some embodiments, an additional beam splitter may be provided in an optical path between imaging system 166 and wavefront sensor 155, and a focusing lens and a detector may be used to create an image of the light incident upon the retina. In that case, the proper or desired adjusted focal length may be determined by minimizing the spot size on the back of the retina, performed by comparing the spot sizes from different focal length values for adjustable focal length lens 169. Beneficially eye 101 is arranged to be one focal length of objective lens 168, and wavefront sensor 155 is arranged to be at the conjugate image plane to eye 101.

Meanwhile, controller/processor 60 receives image data ("first image data") from wavefront sensor 155 produced in response to the light returned from the retina of eye 101 and processes the first image data to determine the refraction of eye 101.

An OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source, a z-scan device 193 operable to alter the focus of the beam in the z-direction (i.e., along the direction of propagation of the OCT beam) under control of the controller, and x-scan device 195, and a y-scan device 197 operable to translate the OCT beam in the x and y directions (i.e., perpendicular to the direction of propagation of the of the OCT beam), respectively, under control of the controller. The OCT light source and reference arm may be incorporated into the main unit 4 of the optical measurement instrument 1 shown in FIG. 8A. Alternatively, the OCT assembly 191 may be housed in a second unit 200 and the OCT beam from the OCT source may be directed from the second housing 200 to the main unit by optical pathway 192.

The OCT systems and methods of the optical measurement instruments and methods described herein may be FD-OCT (Fourier domain optical coherence tomography) systems, including either an SD-OCT (spectral domain optical coherence tomography) system or an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range and collecting all the scattering information at each wavelength and at each position, the composition of the collected signal is equivalent to the spectral-domain OCT technique. The collected spectral data is then inverse Fourier transformed to recover the spatial depth-dependent information.

FD-OCT suffers from an inherent sample-independent limited depth range, typically between 1 and 5 mm. One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero-path length difference (ZPD) position. As a result, the positive and negative displacements about the ZPD cannot be unambiguously resolved, which gives rise to mirror image artifacts and generally halves the useable range. This is referred to as the complex conjugate ambiguity. Another limitation is a sensitivity fall-off which results in reduced sensitivity with increasing depth. Moreover, since the signal in OCT is derived only from backscattered photons, optical attenuation from absorption and scattering generally result in a useable imaging depth of about 1-4 mm.

Figure 11:
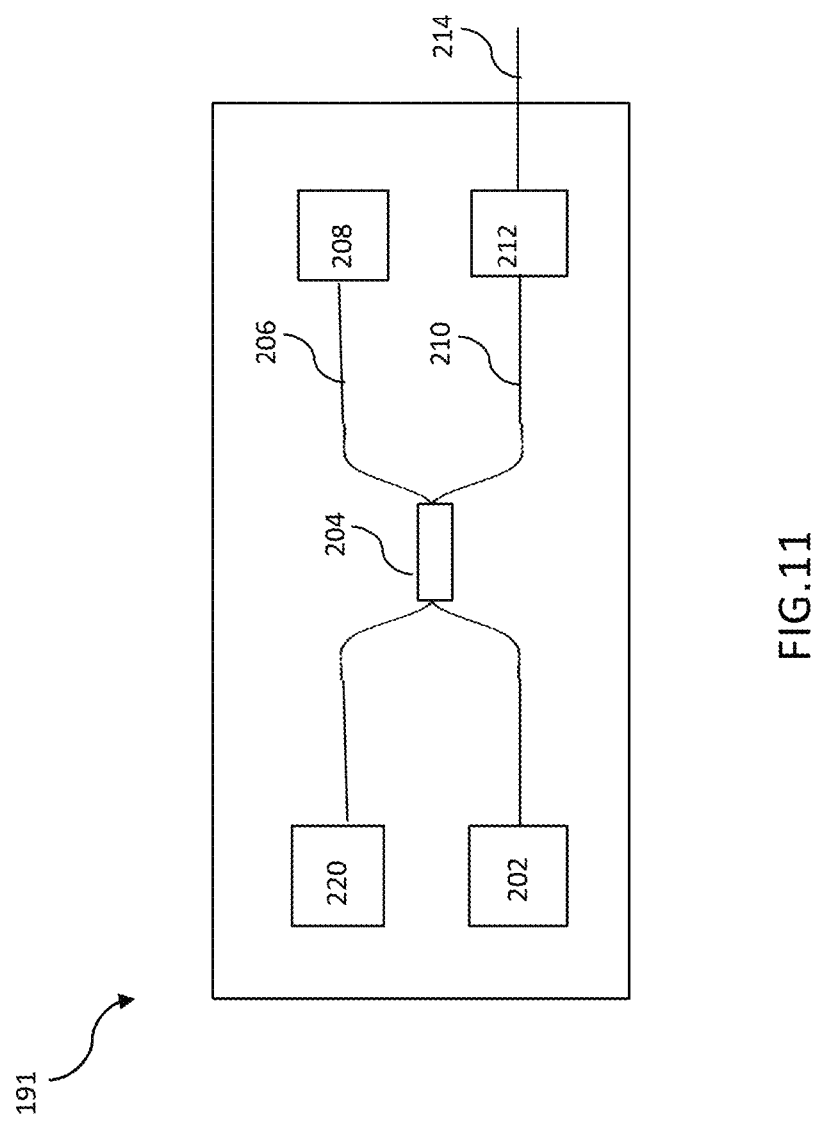
FIG. 11 is a block diagram of an OCT assembly according to many embodiments of the present invention.

Several "full range" OCT techniques have been developed that eliminate the complex conjugate artifacts to effectively double the measurement range around the ZPD position. These full range OCT techniques result in useable imaging depths of up to about 5 mm up to about 8 mm. Suitable full range techniques are methods utilizing a dithering reference lag to break the phase ambiguity, methods that use phase distortion, and other suitable methods As shown in FIG. 11, the OCT assembly 191 of OCT subsystem 190 includes a broadband or a swept light source 202 that is split by a coupler 204 into a reference arm 206 and a sample arm 210. The reference arm 106 includes a module 108 containing a reference reflection along with suitable dispersion and path length compensation. The sample arm 110 of the OCT assembly 191 has an output connector 212 that serves as an interface to the rest of the optical measurement instrument. The return signals from both the reference and sample arms 206, 210 are then directed by coupler 204 to a detection device 220, which employs either time-domain, frequency, or single point detection techniques. In FIG. 11, a swept source technique is used with a laser wavelength of 1060 nm swept over a range of 8-50 mm depth.

Figure 12:
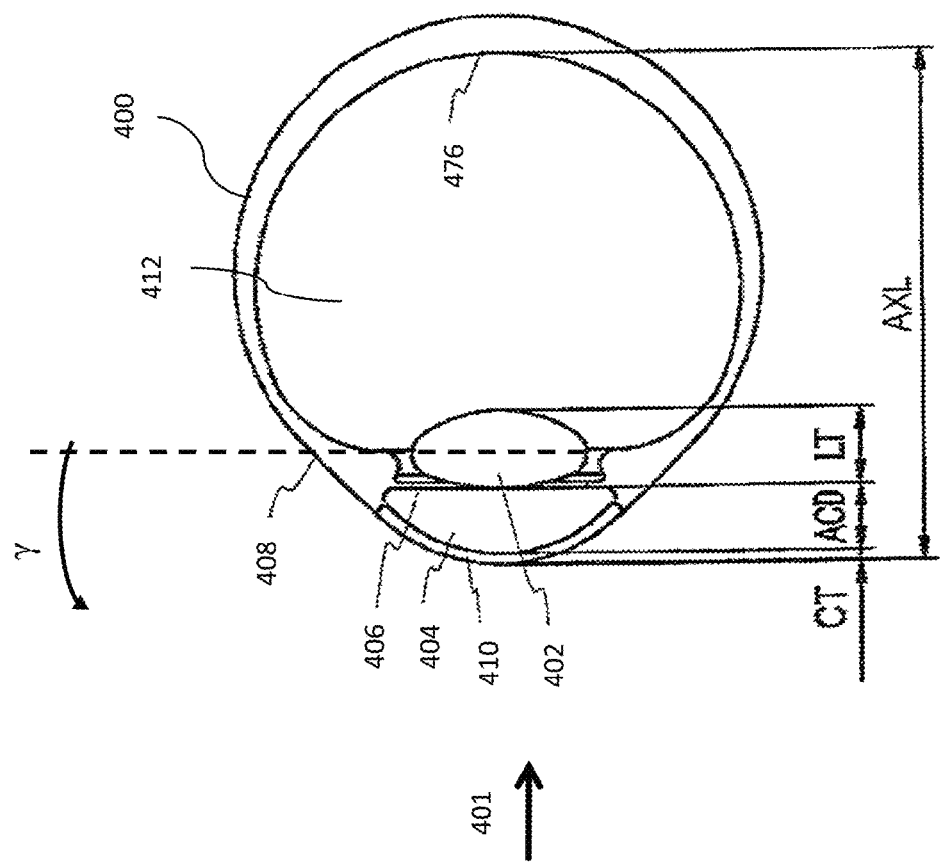
FIG. 12 is a schematic drawing of a human eye.

FIG. 12 is a schematic drawing of a human eye 400. In many embodiments, a light beam 401 from a light source enters the eye from the left of FIG. 12, refracts into the cornea 410, passes through the anterior chamber 404, the iris 406 through the pupil, and reaches lens 402. After refracting into the lens, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 476. As indicated in FIG. 12, cornea 410 has corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 476. FIG. 12 also illustrates that, in many subjects the lens, including the lens capsule, may be tilted at one or more angles relative to the optical axis, including an angle γ relative to the optical axis of the eye.

The optical system may also be arranged so that the movement pattern of the scan mirrors provides a lateral motion across the retina so that the shape of the retina may be determined. It is of specific interest to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases, there may be an absence of a foveal pit that also is considered an indication of a corneal abnormality.

The average axial length of the adult human eye is about 24 mm. Since the full range imaging depth of the OCT measurements are only about 5 mm to 8 mm, then OCT scanning may provide for OCT scans at different depths of the eye that can be combined to form a combined OCT image of the eye. The OCT measurements may include OCT imaging at various depths of the patient's eye for imaging: (1) at least a portion of the retina, (2) at least a portion of the anterior portion of the eye, including at least a portion of the cornea (anterior and posterior), iris, and lens (anterior and posterior), and (3) performing axial eye length measurements.

Figure 13A:
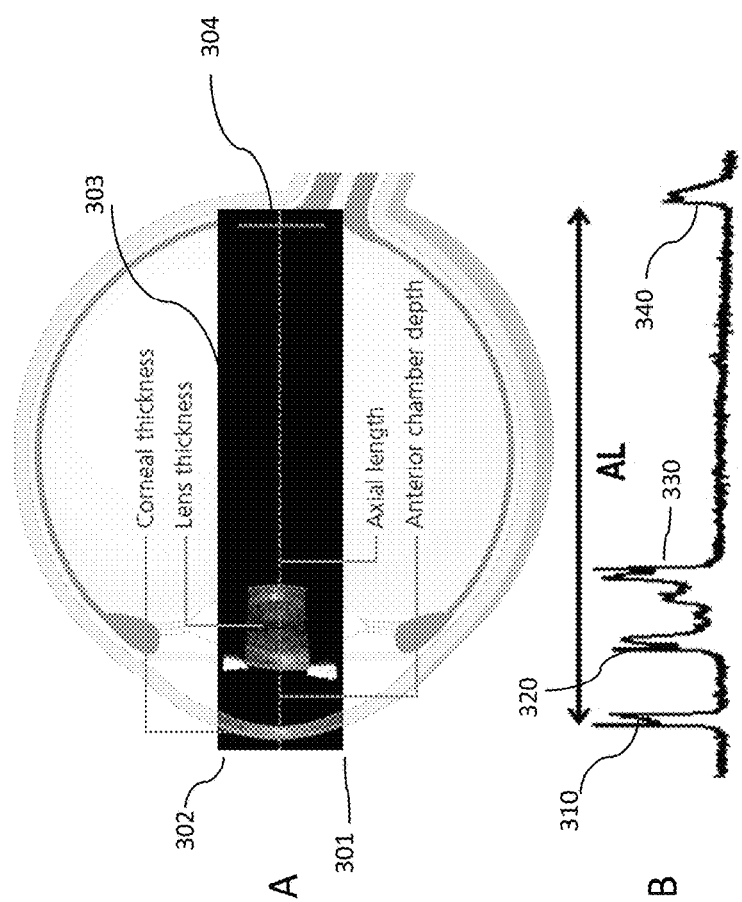
FIG. 13A illustrates a preferred scanning region for the OCT subsystem according to many embodiments of the present invention.
Figure 13B:
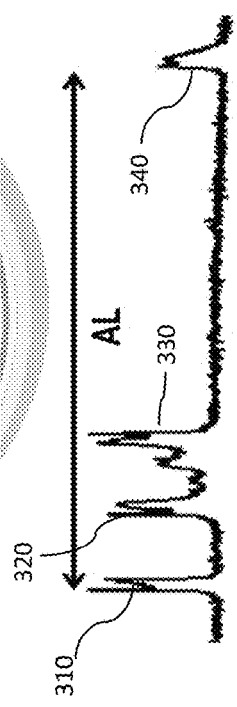
FIG. 13B shows a representative graph of an intensity of an OCT signal of an OCT subsystem according to many embodiments as a function of depth along the axis defining the axial length of the eye.
Figure 13C:
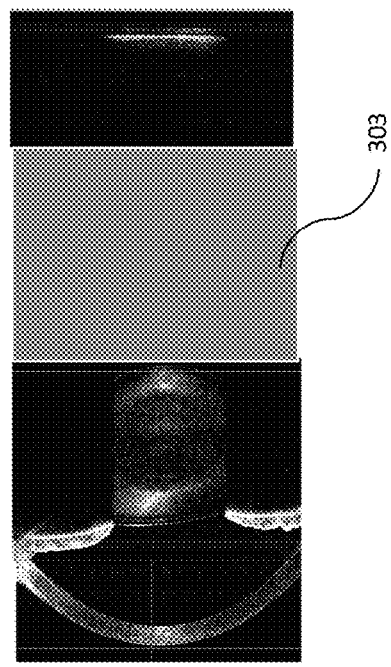
FIG. 13C shows a cross-section of an eye obtained by an optical measurement system of the present invention using an OCT subsystem according to the present invention

FIGS. 13A-13C illustrate various aspects of the OCT subsystem 190 according to various aspects of the present invention. FIG. 13A illustrates a preferred scanning region for the OCT subsystem according to many embodiments of the present invention. The scanning region may be defined from starting point 301 to ending point 302 at the anterior portion of the eye extending in a direction transverse the direction of propagation of the OCT beam, and extending in a direction parallel to an axis defining the axial length of the eye to the posterior portion 304 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 190 because the portion 330 does not contain anatomical structure for 3D analysis.

FIG. 13B shows a representative graph of an intensity of an OCT signal of an OCT subsystem 190 according to many embodiments as a function of depth along the axis defining the axial length of the eye. The graph generally exhibits approximately four peaks having a complex structure: (1) a peak 310 having a doublet-like structure and generally corresponding to a location of the cornea; (2) a peak 320 having a doublet-like structure and generally corresponding to a location of an anterior surface of the lens; (3) a peak 330 having a complex structure generally corresponding to a location of a posterior surface of the lens; and (4) a peak 340 generally corresponding to a location of a retina. A distance between peak 310 and peak 340 can be used to calculate the axial length (AL) of the eye. An OCT scan by OCT subsystem 190, including both an A-scan and B-scan, may be conducted for at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by the OCT subsystem 190, including both an A-Scan and a B-scan is performed at a location corresponding to each of a location of the cornea, a location of an anterior surface of the lens, a location of a posterior surface of the lens, and a location corresponding to a retina.

It should be noted that because the OCT subsystem 190 provides for the detection of various structures of the eye, including a location of the cornea, the OCT subsystem 190 may be used as a ranging system to precisely align the patient in relation to the optical measurement system 1 of the present invention. The use of the OCT as a ranging system can significantly improve accuracy of corneal topography measurements, including keratometry measurements, which are sensitive to misalignment of the corneal structures.

FIG. 13C shows a cross-section of an eye obtained by an optical measurement system of the present invention using an OCT subsystem according to the present invention.

Figure 14:
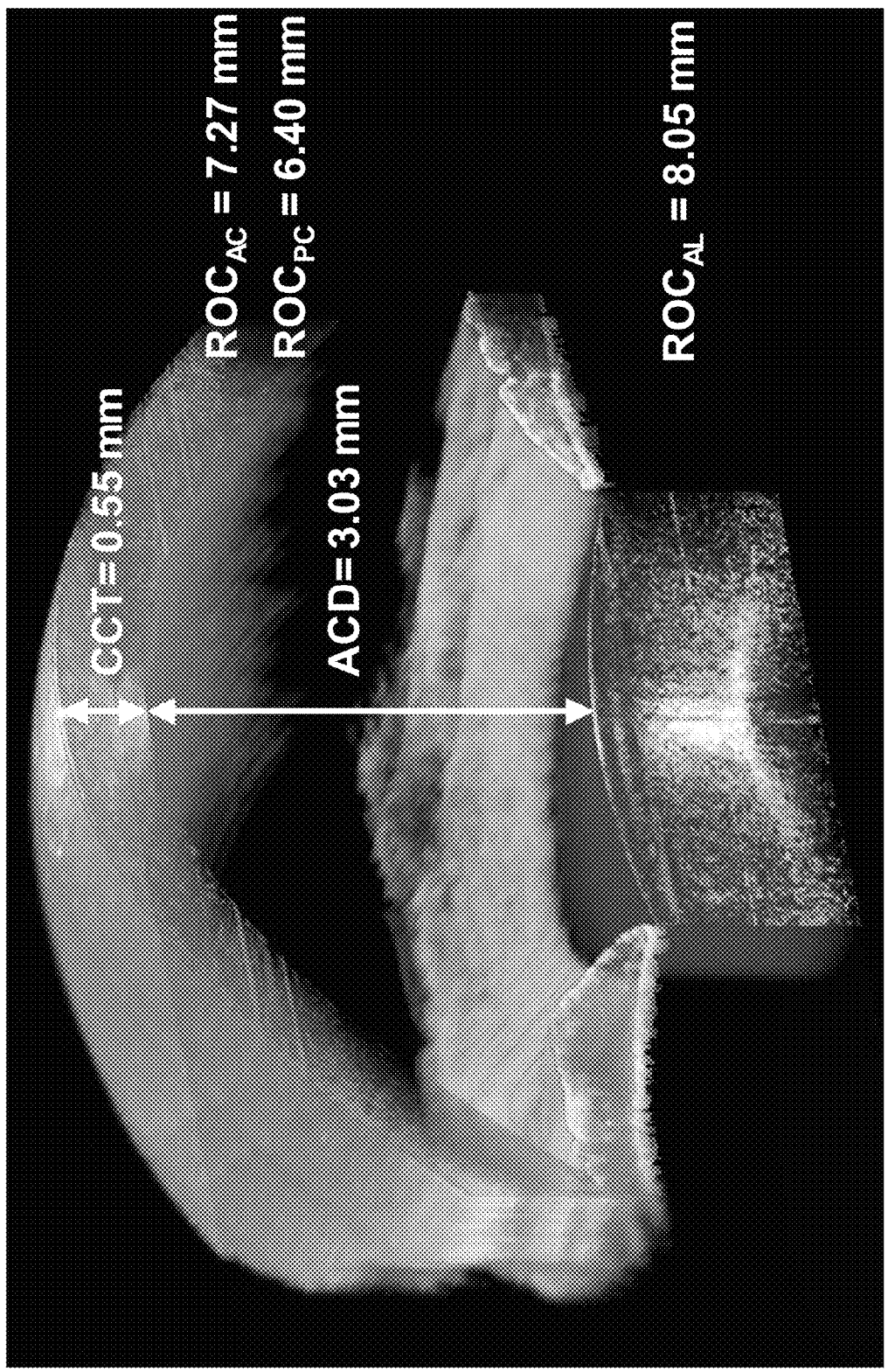
FIG. 14 is a 3-dimensional representation of an anterior portion of an eye obtained using the optical measurement system according to many embodiments.

FIG. 14 shows a 3-dimensional view of an eye obtained by an optical measurement system of the present invention using an OCT subsystem according to the present invention. FIG. 14 evidences that the OCT subsystem of the present invention is operable to obtain biometry measurements according to the present invention, including the central corneal thickness (CCT), the anterior chamber depth (ACD), the radius of curvature of the anterior cornea ($ROC_{AC}$), the radius of curvature of the Posterior cornea ($ROC_{PC}$) and the Radius of curvature of the axial length ($ROC_{AL}$).

OCT subsystem 190 may provide sufficiently resolved structural information to a structural assessment that may provide a user with an indication of suitability of a patient for a laser cataract procedure. In one embodiment, an OCT scan performed by the OCT subsystem 190 at or near the retina (i.e., a retina scan) is sufficiently resolved to identify the foveal pit location and depth, wherein a lack of depression indicates an unhealthy retina.

In another embodiment, the optical measurement instrument 1 of the present invention provides one or more measurements sufficient to provide an assessment of the tear film of a patient. In one embodiment, the tear film assessment comprises a comparison of a wavefront aberrometry map and a corneal topography map or OCT map of the patient's eye, by, for instance, subtracting the corneal topography map from the wavefront aberrometry map, to obtain a difference map. A determination of whether the tear film is broken (if not smooth); an assessment of the tear film, including tear film breakup, can be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable In operation, as shown in FIG. 10A, after exiting connector 212, the OCT beam 214 may be collimated, for example using a collimating optical fiber 196. Following collimating fiber 196 the OCT beam 214 is directed to an z-scan device 193 operable to change the focal point of the OCT beam in a z-direction, and x- and y-scan devices 195 and 197, which are operable to scan the OCT beam in x and y-directions perpendicular to the z-direction.

Following the collimating optical fiber 196, the OCT beam 214 continues through a z-scan device 193, 194. The z-scan device may be a Z telescope 193, which is operable to scan focus position of the laser pulse beam 66 in the patient's eye 101 along the Z axis. For example, the Z-telescope may include a Galilean telescope with two lens groups (each lens group includes one or more lenses). One of the lens groups moves along the Z axis about the collimation position of the Z-telescope 193. In this way, the focus position in the patient's eye 101 moves along the Z axis. In general, there is a relationship between the motion of lens group and the motion of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a z-scan device for changing the focus point of the OCT beam 214 in the patient's eye 101. The Z-scan device can be controlled automatically and dynamically by the controller 60 and selected to be independent or to interplay with the X and Y scan devices described next.

After passing through the z-scan device, the OCT beam 214 is incident upon an X-scan device 195, which is operable to scan the OCT beam 214 in the X direction, which is dominantly transverse to the Z axis and transverse to the direction of propagation of the OCT beam 214. The X-scan device 195 is controlled by the controller 60, and can include suitable components, such as a lens coupled to a MEMS device, a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 196, the OCT beam 214 is incident upon a Y scan device 197, which is operable to scan the OCT beam 214 in the Y direction, which is dominantly transverse to the X and Z axes. The Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 195 and the Y-Scan device 197 can be provided by an XY-scan device configured to scan the laser pulse beam 66 in two dimensions transverse to the Z axis and the propagation direction of the laser pulse beam 66. The X-scan and Y scan devices 195, 197 change the resulting direction of the OCT beam 214, causing lateral displacements of OCT beam 214 located in the patient's eye 101.

The OCT sample beam 214 is then directed to beam splitter 173 through lens 175 through quarter wave plate 171 and aperture 114 and to the patient eye 101. Reflections and scatter off of structures within the eye provide return beams that retrace back through the patient interface quarter wave plate 171, lens 175, beam splitter 173, y-scan device 197, x-scan device 195, z-scan device 193, optical fiber 196 and beam combiner 204 (FIG. 12), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by the controller 60 to determine the spatial disposition of the structures of interest in the patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface.

Optical measurement systems disclosed herein may comprise an iris imaging subsystem 40. The imaging subsystem 40 generally may comprise an infrared light source, for example an infrared light source 152, and detector 141. In operation light from the light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in XY and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 100. The cornea generally magnifies and slightly displaces the image from the physical location of the iris. So, the alignment that is done is to the entrance pupil of the eye. This is generally the desired condition for wavefront sensing and iris registration.

Iris images obtained by the iris imaging subsystem may be used for registering and/or fusing the multiple data sets obtained by the various subsystems of the present invention, by methods described for instance in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, an optical measurement system according the present includes a target fixation system 50 (FIG. 9), and an assembly 100 shown in FIGS. 10A and 10B includes fixation target subsystem 180 which includes optics 186 and a fixation target 182 for the patient to view. Fixation target subsystem 180 is used to control the patient's accommodation for wavefront aberrometry measurements, as described above, and because it is often desired to measure the refraction and wavefront aberrations when eye 100 is focused at its far point (e.g., because LASIK treatments are primarily based on this). In the fixation target subsystem 180, a projection of target 182, for instance a cross-hair pattern, is projected onto the eye 101 of the patient, the cross-hair pattern being formed, for example, by a backlit LED and a film. In other embodiments, target 182 may be formed on a video display device which is included in fixation target subsystem 180.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement to maintain the eye in a fixed focal position.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan is taken at least at the retina, the cornea and one of anterior portion of the patient's lens. An iris image may be taken simultaneously with or sequentially with an each of measurements taken with wavefront aberrometry subsystem the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

FIG. 15 shows one embodiment of an operating sequence and method in which wavefront aberrometry measurements, corneal topography measurements and OCT measurements are all taken. The optical measurement apparatus, including the method of FIG. 15 may be used preoperatively, intraoperatively and/or postoperatively. In the method of FIG. 15, a step 801 comprises aligning the optical measurement system to the eye of the patent. A step 805 comprises activating the fixation target subsystem for patient fixation on target. A step 810 comprises activating the wavefront aberrometer subsystem such that the wavefront aberrometer light source 810 is activated and the eye refraction is measured via the wavefront sensor. A step 815 comprises activating the fixation target system to move the target to an optimum position and activate the wavefront aberrometer subsystem such that the wavefront aberrometer light source 152 is activated and the eye refraction is measured via the wavefront sensor 155. A step 820 comprises obtaining an iris image using Iris Imaging Subsystem 40 while infrared light source 152 is operating. A step 825 comprises operating the z-scan device to set OCT scan location at or near cornea and performing an OCT Scan with the OCT Subsystem. A step 830 comprises operating the z-scan device to set the OCT location at a location at or near the lens anterior and performing an OCT Scan with the OCT Subsystem. A step 835 comprises operating the z-scan device to set the OCT location at a location at or near the lens posterior and performing an OCT Scan with the OCT Subsystem. A step 840 comprises operating the X-scan device and Y-scan device so no light from OCT reaches detector 141. A step 845 comprises obtaining an iris image using the Iris Imaging Subsystem while the infrared light source 152 flashes. A step 850 comprises obtaining an iris image using the Iris Imaging Subsystem while the light sources 120 and Helmholz source flash. A step 855 comprises measuring the corneal topography with the Corneal Topography Subsystem. A step 855 comprises operating the z-scan device to set the OCT location at a location at or near the retina and performing an OCT Scan with the OCT Subsystem. A step 860 comprises operating the X-scan device and Y-scan device so no light from OCT reaches detector 141. An optional step 865 comprises measuring corneal topography with Corneal Topography Subsystem, which may provide for an improved 3D model of the patient eye. An optional step 870 comprises obtaining an iris image using Iris Imaging Subsystem (for 3D model).

The optical measurement instrument 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement instrument 1, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

The optical measurement instrument 1 and the optical measurements obtained therewith may be used intra-operatively, i.e., during a cataract surgery or other surgical procedure, for, e.g., intraoperative eye diagnostics, determining IOL placement and position, surgical planning, and control/ or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement instrument 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

The optical measurement instrument 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

The optical measurement instrument 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement instrument 1, in conjunction with measurement data of a subject's eye obtained by optical measurement instrument 1, for cataract diagnostics or cataract treatment planning, which may include specifying and/or selecting a specific IOL for a subject's eye. For example, one or more processors of optical measurement instrument 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement instrument 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, comprises: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, comprising: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device storing computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position comprising: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, the system comprising: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

A method for planning a refractive treatment of an eye of a patient comprises: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, comprises: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a postoperative condition of the eye based at least partially on the measured eye characteristics; and predictively estimating, in accordance with an output of said empirically calculating and the eye characteristics, the at least one parameter of the intraocular lens to obtain the desired postoperative condition.

A method of adjusting the refractive power in an eye of a patient who has undergone cataract surgery comprises: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system, comprising:
   a wavefront aberrometer configured to measure a refraction of an eye;
   at least one processor;
   a first movable stage, wherein the first movable stage is movable with respect to the eye under control of the at least one processor;
   a second movable stage mounted on the first movable stage, wherein the second movable stage is independently movable with respect to the first movable stage and with respect to the eye, under control of the at least one processor;
   a fixation target for presentation by the system to the eye to cause the eye to accommodate during a process of measuring the refraction of the eye, wherein the fixation target is disposed on the second movable stage; and
   an optical system disposed in an optical path between the fixation target and the eye, wherein the optical system includes:
      a first lens which is not disposed on the first stage or second stage,
      a second lens and a third lens, each disposed on the first stage and not disposed on the second stage,
      a fourth lens disposed on the second stage and stationary relative to the fixation target, and
      a Stokes cell disposed on the first stage in the optical path between the second lens and the third lens.

2. The system of claim 1, wherein the Stokes cell is disposed one focal length from the second lens.

3. The system of claim 2, wherein a focal length of the fourth lens is about one half the focal length of the third lens.

4. The system of claim 1, wherein at least one of the third lens and the fourth lens comprises one of a telephoto lens and a retrofocus lens, including a weaker negative element combined with a stronger positive element.

5. The system of claim 1, further comprising a video display, wherein the fixation target is provided via the video display, and wherein the at least one processor is configured to electronically make a size of the fixation target on the video display smaller while moving the second movable stage away from the eye.

6. The system of claim 1, wherein the aberrometer comprises:
   a light source;
   a Shack-Hartmann wavefront sensor; and
   a pair of lenses arranged as a telescope and configured to deliver a probe beam to the eye and returning light from the eye to the Shack-Hartmann wavefront sensor for measuring the refraction of the eye,
   wherein the Shack-Hartmann wavefront sensor and a first one of the pair of lenses is disposed on the first stage, and wherein a second one of the pair of lenses is not disposed on the first stage or the second stage.

7. The system of claim 1, wherein the fixation target comprises a circular pattern with a pair of cross hairs crossing at a middle of the circular pattern.

8. A method, comprising:
   providing an arrangement comprising:
      a first movable stage, wherein the first movable stage is movable under control of at least one processor with respect to an eye of a subject,
      a second movable stage disposed on the first movable stage, wherein the second movable stage is independently movable with respect to the first movable stage and with respect to the eye, under control of the at least one processor,
      a fixation target disposed on the second movable stage, and
      an optical system disposed in an optical path between the fixation target and the eye, wherein the optical system includes a Stoke cell and projects the fixation target upon the eye;
   the at least one processor moving the first movable stage with respect to the eye to a first stage position where the fixation target draws a focus of the eye to near its far point;
   stopping movement of the first movable stage with respect to the eye at the first stage position; and
   while the first movable stage is stopped, moving the second movable stage with respect to the first movable stage and the eye to a second stage position where the fixation target is moved away from the eye by an additional amount such that blur cues of the fixation target indicate to the subject that the fixation target is moving away from the eye at a same time that a size of an image of the fixation target on a retina of the eye decreases;
   measuring a cylinder of the eye;
   adjusting the Stokes cell to compensate for the measured cylinder of the eye;
   the at least one processor moving the first movable stage again with respect to the eye to the first stage position where the fixation target draws a focus of the eye to near its far point;
   again stopping movement of the first movable stage with respect to the eye at the first stage position; and
   while the first movable stage is stopped, moving the second movable stage again with respect to the first movable stage and the eye to another second stage position where the fixation target is moved away from the eye by another additional amount such that blur cues of the fixation target indicate to the subject that the fixation target is moving away from the eye at a same time that the size of the image of the fixation target on the retina of the eye decreases;
   measuring a refraction of the eye.

9. The method of claim 8, wherein the optical system non-telecentrically projects the fixation target upon the eye.

10. The method of claim 9, further comprising measuring the cylinder of the eye with a wavefront aberrometer having a wavefront sensor and a telescope, wherein a first lens of the telescope is disposed on the first stage and a second lens of the telescope is not disposed on the first stage or the second stage.

11. The method of claim 9, wherein the fixation target comprises a circular pattern with a pair of cross hairs crossing at a middle of the circular pattern.

12. The method of claim 9,
   wherein the optical system comprises:
      at least a first lens which is not disposed on the first stage or second stage,
      a second lens and a third lens, each disposed on the first stage and not disposed on the second stage, and
      a fourth lens disposed on the second stage,
      wherein the Stokes cell is disposed on the first stage in the optical path between the second lens and the third lens,
   further comprising measuring the cylinder of the eye with a wavefront aberrometer having a wavefront sensor and a telescope, wherein a first lens of the telescope is disposed on the first stage and a second lens of the telescope is not disposed on the first stage or the second stage.

13. The method of claim 9, wherein the fixation target is provided via a video display, and wherein the method comprises electronically making a size of the fixation target on the video display smaller while moving the second movable stage to the second stage position.

14. A system, comprising:
- a first movable stage, wherein the first movable stage is movable under control of the at least one processor with respect to an eye of a subject;
- a second movable stage mounted on the first movable stage, wherein the second movable stage is independently movable with respect to the first movable stage and with respect to the eye, under control of the at least one processor;
- a fixation target which is disposed on the second movable stage; and
- an optical system disposed in an optical path between the fixation target and the eye, wherein the optical system is configured for projecting the fixation target upon the eye to accommodate the eye,
- wherein the optical system includes a Stokes cell in the optical path between the fixation target and the eye, and
- wherein the optical system non-telecentrically projects an image of the fixation target upon a retina of the eye and a size of the image of the fixation target on the retina become smaller as the fixation target is moved further away from eye by the second stage.

15. The system of claim 14, wherein the optical system comprises at least a first lens which is not disposed on the first stage or second stage.

16. The system of claim 14, wherein the optical system comprises at least a second lens which is disposed on the second stage.

17. The system of claim 14, wherein the optical system comprises:
- at least a first lens which is not disposed on the first stage or second stage,
- a second lens and a third lens, each disposed on the first stage and not disposed on the second stage, and
- a fourth lens disposed on the second stage,
- wherein the Stokes cell is disposed on the first stage in the optical path between the second lens and the third lens.

18. The system of claim 17, wherein the Stokes cell is disposed one focal length from the second lens.

19. The system of claim 17, wherein a focal length of the fourth lens is about one half the focal length of the third lens.

20. The system of claim 14, further comprising a video display, wherein the fixation target is provided via the video display, and wherein the at least one processor is configured to electronically make a size of the fixation target on the video display smaller while moving the second movable stage to the second stage position.

* * * * *